US009265428B2

(12) United States Patent
O'Brien et al.

(10) Patent No.: US 9,265,428 B2
(45) Date of Patent: *Feb. 23, 2016

(54) IMPLANTABLE WIRELESS SENSOR

(75) Inventors: David O'Brien, Norcross, GA (US);
Jason White, Smyrna, GA (US);
Michael A. Fonseca, Marietta, GA (US);
Jason Kroh, Villa Rica, GA (US); Mark Allen, Atlanta, GA (US); David Stern, Grayson, GA (US)

(73) Assignee: ST. JUDE MEDICAL LUXEMBOURG HOLDINGS II S.A.R.L. ("SJM LUX II"), Luxembourg (LU)

( * ) Notice: Subject to any disclaimer, the term of this patent is extended or adjusted under 35 U.S.C. 154(b) by 1505 days.

This patent is subject to a terminal disclaimer.

(21) Appl. No.: 12/175,803

(22) Filed: Jul. 18, 2008

(65) Prior Publication Data

US 2009/0030291 A1 Jan. 29, 2009

Related U.S. Application Data

(62) Division of application No. 11/472,905, filed on Jun. 22, 2006, now Pat. No. 7,574,792, which is a division of application No. 10/943,772, filed on Sep. 16, 2004, now abandoned.

(60) Provisional application No. 60/503,745, filed on Sep. 16, 2003.

(51) Int. Cl.
*A61B 5/02* (2006.01)
*A61B 5/00* (2006.01)
*A61B 5/07* (2006.01)

(52) U.S. Cl.
CPC ........... *A61B 5/02014* (2013.01); *A61B 5/0031* (2013.01); *A61B 5/076* (2013.01); *Y10T 29/49016* (2015.01); *Y10T 29/49069* (2015.01); *Y10T 29/49071* (2015.01); *Y10T 29/49073* (2015.01)

(58) Field of Classification Search
None
See application file for complete search history.

(56) References Cited

U.S. PATENT DOCUMENTS

| | | | |
|---|---|---|---|
| 2,512,641 A | 6/1950 | Halstead | |
| 2,769,863 A | 6/1957 | Von Wittern | |
| 3,350,944 A | 11/1967 | De Michele | |
| 3,419,384 A | 12/1968 | Rembaum | |
| 3,419,834 A | 12/1968 | McKechnie et al. | |
| 3,550,137 A | 12/1970 | Kuecken | |
| 3,651,243 A | 3/1972 | Hornor et al. | |
| 3,867,950 A | 2/1975 | Fischell | |
| 3,882,424 A | 5/1975 | Debois et al. | |
| 3,913,028 A | 10/1975 | Bosselaers | |
| 3,942,382 A | 3/1976 | Hok | |
| 3,958,558 A | 5/1976 | Dunphy et al. | |
| 4,026,276 A | 5/1977 | Chubbuck | |
| 4,077,016 A | 2/1978 | Sanders et al. | |
| 4,114,606 A | 9/1978 | Seylar | |
| 4,127,110 A | 11/1978 | Bullara | |
| 4,152,669 A | 5/1979 | Igarashi | |
| 4,206,762 A | 6/1980 | Cosman | |
| 4,207,604 A * | 6/1980 | Bell ............................ 361/283.4 |
| 4,207,903 A | 6/1980 | O'Neill | |
| RE30,366 E | 8/1980 | Rasor et al. | |
| 4,237,900 A | 12/1980 | Schulman et al. | |
| 4,281,212 A | 7/1981 | Bogese, II | |
| 4,354,506 A | 10/1982 | Sakaguchi et al. | |
| 4,378,809 A | 4/1983 | Cosman | |
| 4,385,636 A | 5/1983 | Cosman | |
| 4,389,895 A * | 6/1983 | Rud, Jr. ............................ 73/724 |
| 4,407,296 A * | 10/1983 | Anderson ...................... 600/488 |
| 4,424,403 A | 1/1984 | Bogese, II | |
| 4,467,138 A | 8/1984 | Brorein | |
| 4,485,813 A | 12/1984 | Anderson et al. | |
| 4,494,950 A | 1/1985 | Fischell | |
| 4,521,684 A | 6/1985 | Gilby et al. | |
| 4,531,526 A | 7/1985 | Genest | |
| 4,593,703 A | 6/1986 | Cosman | |
| 4,596,563 A | 6/1986 | Pande | |
| 4,617,606 A | 10/1986 | Shak et al. | |
| 4,617,932 A | 10/1986 | Kornberg | |
| 4,625,561 A * | 12/1986 | Mikkor ............................ 73/724 |

(Continued)

FOREIGN PATENT DOCUMENTS

AU 701577 B2 2/1999
AU 2004274005 A1 3/2005

(Continued)

OTHER PUBLICATIONS

Resonant Beam Pressure Sensor Fabricated with Silicon Fusion Bonding, IEEE, pp. 664-667, dated May 1991 to Peterson, et al.*
A. Dehennis, K.D. Wise; "A Passive-Telemetry-Based Pressure Sensing System": NSF Engineering Research Center for Wireless Integrated Microsystems; Department of Electrical Engineering and Computer Science; The University of Michigan, Ann Arbor, MI 48109-2122 US.
S.R. Vallabhane, J. Brennan, G. Gilling-Smith, D. Gould, T. How, R. McWilliams, P.L. Harris; "Aortic Side Branch perfusion Alone Does Not Account for High Intra-Sac Pressure After Endovascular Repair (EVAR) In the Absence of Graft-Related Endoleak"; Royal Liverpool University Hospital, Liverpool, UK.

(Continued)

*Primary Examiner* — Ann Lam

(57) ABSTRACT

A wireless sensor for indicating a physical state within an environment includes a housing defining a hermetically sealed cavity. A structure located within the cavity of the housing has elements providing capacitance, the elements being arranged such that the distance and thereby the capacitance of the structure changes when a physical state of the environment changes. The structure has a resonant frequency based at least in part on the capacitance of the structure when in the presence of a fluctuating electromagnetic field. When the sensor is positioned within an environment and is subjected to a fluctuating electromagnetic field, the resonant frequency indicates the physical state of the environment.

19 Claims, 19 Drawing Sheets

(56) References Cited

U.S. PATENT DOCUMENTS

| | | | |
|---|---|---|---|
| 4,627,079 A | 12/1986 | von der Embse | |
| 4,651,571 A | 3/1987 | McGlade | |
| 4,660,568 A | 4/1987 | Cosman | |
| 4,679,560 A | 7/1987 | Galbraith | |
| 4,689,806 A | 8/1987 | von der Embse | |
| 4,701,826 A | 10/1987 | Mikkor | |
| 4,713,540 A | 12/1987 | Gilby et al. | |
| 4,718,425 A | 1/1988 | Tanaka et al. | |
| 4,720,687 A | 1/1988 | Ostoich et al. | |
| 4,773,972 A | 9/1988 | Mikkor | |
| 4,796,641 A | 1/1989 | Mills et al. | |
| 4,815,472 A | 3/1989 | Wise et al. | |
| 4,831,325 A * | 5/1989 | Watson, Jr. | 324/678 |
| 4,833,920 A | 5/1989 | Knecht et al. | |
| 4,846,191 A | 7/1989 | Brockway et al. | |
| 4,890,623 A | 1/1990 | Cook et al. | |
| 4,899,752 A | 2/1990 | Cohen | |
| 4,905,575 A | 3/1990 | Knecht et al. | |
| 4,913,147 A | 4/1990 | Fahlstrom et al. | |
| 4,924,172 A | 5/1990 | Holmgren | |
| 4,934,369 A | 6/1990 | Maxwell | |
| 4,987,897 A | 1/1991 | Funke | |
| 5,036,854 A | 8/1991 | Schollmeyer et al. | |
| 5,043,531 A | 8/1991 | Gutenson et al. | |
| 5,113,868 A | 5/1992 | Wise et al. | |
| 5,115,128 A | 5/1992 | Cook | |
| 5,129,394 A | 7/1992 | Mehra | |
| 5,148,123 A | 9/1992 | Ries | |
| 5,153,583 A | 10/1992 | Murdoch | |
| 5,165,289 A | 11/1992 | Tilmans | |
| 5,173,836 A | 12/1992 | Tomase et al. | |
| 5,181,423 A | 1/1993 | Philipps et al. | |
| 5,192,314 A | 3/1993 | Daskalakis | |
| 5,200,930 A | 4/1993 | Rouquette | |
| 5,207,103 A | 5/1993 | Wise et al. | |
| 5,265,606 A | 11/1993 | Kujawski | |
| 5,277,068 A | 1/1994 | Fukiura et al. | |
| 5,312,674 A | 5/1994 | Haertling et al. | |
| 5,313,953 A | 5/1994 | Yomtov et al. | |
| 5,331,453 A | 7/1994 | Lipsky | |
| 5,353,800 A | 10/1994 | Pohndorf et al. | |
| 5,355,714 A | 10/1994 | Suzuki et al. | |
| 5,357,253 A | 10/1994 | Van Etten et al. | |
| 5,373,852 A | 12/1994 | Harrison et al. | |
| 5,400,535 A | 3/1995 | Schomaker | |
| 5,411,535 A | 5/1995 | Fujii et al. | |
| 5,411,551 A | 5/1995 | Winston et al. | |
| 5,431,171 A | 7/1995 | Harrison et al. | |
| 5,440,300 A | 8/1995 | Spillman, Jr. | |
| 5,483,834 A * | 1/1996 | Frick | 73/724 |
| 5,487,760 A | 1/1996 | Villafana | |
| 5,491,299 A | 2/1996 | Naylor et al. | |
| 5,497,099 A | 3/1996 | Walton | |
| 5,515,041 A | 5/1996 | Spillman, Jr. | |
| 5,535,752 A | 7/1996 | Halperin et al. | |
| 5,538,005 A | 7/1996 | Harrison et al. | |
| 5,543,349 A * | 8/1996 | Kurtz et al. | 438/51 |
| 5,551,427 A | 9/1996 | Altman | |
| 5,554,139 A | 9/1996 | Okajima | |
| 5,566,676 A | 10/1996 | Rosenfeldt et al. | |
| 5,574,470 A | 11/1996 | de Vall | |
| 5,593,430 A | 1/1997 | Renger | |
| 5,594,389 A | 1/1997 | Kiyanagi et al. | |
| 5,600,245 A | 2/1997 | Yamamoto et al. | |
| 5,625,341 A | 4/1997 | Giles et al. | |
| 5,626,630 A | 5/1997 | Markowitz et al. | |
| 5,659,155 A | 8/1997 | Porzilli | |
| 5,686,841 A | 11/1997 | Stolarczyk et al. | |
| 5,695,155 A | 12/1997 | Macdonald et al. | |
| 5,701,121 A | 12/1997 | Murdoch | |
| 5,702,427 A | 12/1997 | Ecker et al. | |
| 5,703,412 A | 12/1997 | Takemoto et al. | |
| 5,703,576 A | 12/1997 | Spillman, Jr. et al. | |
| 5,713,917 A | 2/1998 | Leonhardt et al. | |
| 5,722,414 A | 3/1998 | Archibald et al. | |
| 5,723,791 A | 3/1998 | Koch et al. | |
| 5,740,594 A | 4/1998 | Lukasiewicz et al. | |
| 5,743,267 A | 4/1998 | Nikolic et al. | |
| 5,750,926 A | 5/1998 | Schulman et al. | |
| 5,796,827 A | 8/1998 | Coppersmith et al. | |
| 5,807,265 A | 9/1998 | Itoigawa et al. | |
| 5,836,886 A | 11/1998 | Itoigawa et al. | |
| 5,860,938 A | 1/1999 | Lafontaine et al. | |
| 5,896,113 A | 4/1999 | O'Neill, Jr. | |
| 5,899,927 A | 5/1999 | Ecker et al. | |
| 5,935,084 A | 8/1999 | Southworth | |
| 5,942,991 A | 8/1999 | Gaudreau et al. | |
| 5,967,986 A | 10/1999 | Cimochowski et al. | |
| 5,974,894 A | 11/1999 | Delatorre | |
| 5,976,070 A | 11/1999 | Ono et al. | |
| 5,986,549 A | 11/1999 | Teodorescu | |
| 6,009,350 A | 12/1999 | Renken | |
| 6,015,386 A | 1/2000 | Kensey et al. | |
| 6,015,387 A | 1/2000 | Schwartz et al. | |
| 6,019,729 A | 2/2000 | Itoigawa et al. | |
| 6,024,704 A | 2/2000 | Meador et al. | |
| 6,025,725 A | 2/2000 | Gershenfeld et al. | |
| 6,030,413 A | 2/2000 | Lazarus | |
| 6,033,366 A | 3/2000 | Brockway et al. | |
| 6,051,866 A * | 4/2000 | Shaw et al. | 257/417 |
| 6,053,873 A | 4/2000 | Govari et al. | |
| 6,076,016 A | 6/2000 | Feierbach | |
| 6,111,520 A | 8/2000 | Allen et al. | |
| 6,113,553 A | 9/2000 | Chubbuck | |
| 6,134,461 A | 10/2000 | Say et al. | |
| 6,140,740 A | 10/2000 | Porat et al. | |
| 6,159,156 A | 12/2000 | Van Bockel | |
| 6,165,135 A | 12/2000 | Neff | |
| 6,198,965 B1 | 3/2001 | Penner et al. | |
| 6,201,980 B1 | 3/2001 | Darrow et al. | |
| 6,206,835 B1 | 3/2001 | Spillman, Jr. et al. | |
| 6,208,305 B1 | 3/2001 | King | |
| 6,212,056 B1 | 4/2001 | Gammel et al. | |
| 6,237,398 B1 | 5/2001 | Porat et al. | |
| 6,239,724 B1 | 5/2001 | Doron et al. | |
| 6,252,163 B1 | 6/2001 | Fujimori et al. | |
| 6,252,481 B1 | 6/2001 | Iwao et al. | |
| 6,277,078 B1 | 8/2001 | Porat et al. | |
| 6,278,379 B1 | 8/2001 | Allen et al. | |
| 6,287,253 B1 | 9/2001 | Ortega et al. | |
| 6,291,343 B1 | 9/2001 | Tseng et al. | |
| 6,292,104 B1 | 9/2001 | Wakabayashi | |
| 6,298,271 B1 | 10/2001 | Weijand | |
| 6,319,208 B1 | 11/2001 | Abita et al. | |
| 6,327,319 B1 | 12/2001 | Hietala et al. | |
| 6,331,792 B1 | 12/2001 | Tonietto | |
| 6,338,284 B1 | 1/2002 | Najafi et al. | |
| 6,373,264 B1 | 4/2002 | Matsumoto et al. | |
| 6,383,144 B1 | 5/2002 | Mooney et al. | |
| 6,409,674 B1 | 6/2002 | Brockway et al. | |
| 6,411,130 B1 | 6/2002 | Gater | |
| 6,416,474 B1 | 7/2002 | Penner et al. | |
| 6,442,413 B1 | 8/2002 | Silver | |
| 6,448,500 B1 | 9/2002 | Hosaka et al. | |
| 6,454,720 B1 | 9/2002 | Clerc et al. | |
| 6,495,895 B1 | 12/2002 | Peterson et al. | |
| 6,517,483 B2 | 2/2003 | Park et al. | |
| 6,533,733 B1 | 3/2003 | Hylton et al. | |
| 6,548,176 B1 | 4/2003 | Gwo | |
| 6,577,893 B1 | 6/2003 | Besson et al. | |
| 6,625,341 B1 | 9/2003 | Novotny | |
| 6,645,143 B2 | 11/2003 | VanTassel et al. | |
| 6,656,135 B2 | 12/2003 | Zogbi et al. | |
| 6,660,564 B2 | 12/2003 | Brady | |
| 6,667,725 B1 | 12/2003 | Simons et al. | |
| 6,678,458 B2 | 1/2004 | Ellis et al. | |
| 6,682,490 B2 | 1/2004 | Roy et al. | |
| 6,689,056 B1 | 2/2004 | Kilcoyne et al. | |
| 6,702,983 B2 | 3/2004 | Hu et al. | |
| 6,706,005 B2 | 3/2004 | Roy et al. | |
| 6,743,173 B2 | 6/2004 | Penner et al. | |
| 6,743,183 B1 | 6/2004 | Thornton | |
| 6,749,574 B2 | 6/2004 | O'Keefe | |
| 6,765,493 B2 | 7/2004 | Lonsdale et al. | |

(56) References Cited

U.S. PATENT DOCUMENTS

| | | |
|---|---|---|
| 6,777,940 B2 | 8/2004 | Macune |
| 6,812,404 B1 | 11/2004 | Martinez |
| 6,822,570 B2 | 11/2004 | Dimmer et al. |
| 6,827,250 B2 | 12/2004 | Uhland et al. |
| 6,837,438 B1 | 1/2005 | Takasugi et al. |
| 6,855,115 B2 | 2/2005 | Fonseca et al. |
| 6,870,105 B2 | 3/2005 | Maydanich et al. |
| 6,890,300 B2 * | 5/2005 | Lloyd et al. .............. 600/398 |
| 6,895,281 B1 | 5/2005 | Amundson et al. |
| 6,898,454 B2 | 5/2005 | Atalar et al. |
| 6,918,173 B2 | 7/2005 | Ahn |
| 6,919,240 B2 | 7/2005 | Uzawa et al. |
| 6,923,769 B2 | 8/2005 | Nishii et al. |
| 6,926,670 B2 | 8/2005 | Rich et al. |
| 6,929,974 B2 | 8/2005 | Ding et al. |
| 6,939,299 B1 * | 9/2005 | Petersen et al. .............. 600/398 |
| 6,943,419 B2 | 9/2005 | Wong et al. |
| 6,943,688 B2 | 9/2005 | Chung et al. |
| 6,968,743 B2 | 11/2005 | Rich et al. |
| 6,989,493 B2 | 1/2006 | Hipwell, Jr. et al. |
| 7,005,056 B2 | 2/2006 | Srinivasan et al. |
| 7,024,936 B2 | 4/2006 | Pedersen et al. |
| 7,048,756 B2 | 5/2006 | Eggers et al. |
| 7,049,523 B2 | 5/2006 | Shuman et al. |
| 7,060,038 B2 | 6/2006 | Letort et al. |
| 7,076,215 B1 | 7/2006 | Moliere |
| 7,092,765 B2 | 8/2006 | Geske et al. |
| 7,147,604 B1 | 12/2006 | Allen et al. |
| 7,152,477 B2 | 12/2006 | Banholzer et al. |
| 7,181,261 B2 | 2/2007 | Silver et al. |
| 7,208,684 B2 | 4/2007 | Fetterolf, Sr. et al. |
| 7,215,991 B2 | 5/2007 | Besson et al. |
| 7,233,182 B1 | 6/2007 | Savoj |
| 7,245,117 B1 | 7/2007 | Joy et al. |
| 7,250,041 B2 | 7/2007 | Chiu et al. |
| 7,256,695 B2 | 8/2007 | Hamel et al. |
| 7,265,478 B2 | 9/2007 | Thiesen |
| 7,309,330 B2 | 12/2007 | Bertrand et al. |
| 7,353,711 B2 | 4/2008 | O'Dowd et al. |
| 7,425,200 B2 | 9/2008 | Brockway et al. |
| 7,432,723 B2 | 10/2008 | Ellis et al. |
| 7,439,723 B2 | 10/2008 | Allen et al. |
| 7,466,120 B2 | 12/2008 | Miller et al. |
| 7,498,799 B2 | 3/2009 | Allen et al. |
| 7,550,978 B2 | 6/2009 | Joy et al. |
| 7,572,228 B2 | 8/2009 | Wolinsky et al. |
| 7,574,492 B2 | 8/2009 | Karaoguz et al. |
| 7,574,792 B2 | 8/2009 | O'Brien et al. |
| 7,595,647 B2 | 9/2009 | Kroh et al. |
| 7,621,036 B2 | 11/2009 | Cros et al. |
| 7,621,878 B2 | 11/2009 | Ericson et al. |
| 7,647,836 B2 | 1/2010 | O'Brien et al. |
| 7,662,653 B2 | 2/2010 | O'Brien et al. |
| 7,679,355 B2 | 3/2010 | Allen et al. |
| 7,699,059 B2 | 4/2010 | Fonseca et al. |
| 7,699,060 B2 | 4/2010 | Behm |
| 7,748,277 B2 | 7/2010 | O'Brien et al. |
| 7,839,153 B2 | 11/2010 | Joy et al. |
| 7,930,032 B2 | 4/2011 | Teske et al. |
| 7,932,732 B2 | 4/2011 | Ellis et al. |
| 7,936,174 B2 | 5/2011 | Ellis et al. |
| 7,973,540 B2 | 7/2011 | Kroh et al. |
| 8,025,625 B2 | 9/2011 | Allen |
| 8,026,692 B2 | 9/2011 | Chang |
| 8,026,729 B2 | 9/2011 | Kroh et al. |
| 8,083,741 B2 | 12/2011 | Morgan et al. |
| 8,140,168 B2 | 3/2012 | Olson et al. |
| 8,237,451 B2 | 8/2012 | Joy et al. |
| 8,278,941 B2 | 10/2012 | Kroh et al. |
| 2001/0001311 A1 | 5/2001 | Park et al. |
| 2002/0013994 A1 | 2/2002 | Ahn |
| 2002/0049394 A1 | 4/2002 | Roy et al. |
| 2002/0052563 A1 | 5/2002 | Penn et al. |
| 2002/0075825 A1 | 6/2002 | Hills et al. |
| 2002/0087059 A1 | 7/2002 | O'keefe |
| 2002/0115920 A1 | 8/2002 | Rich et al. |
| 2002/0138009 A1 * | 9/2002 | Brockway et al. .............. 600/485 |
| 2002/0147416 A1 | 10/2002 | Zogbi et al. |
| 2002/0151816 A1 | 10/2002 | Rich et al. |
| 2002/0170897 A1 | 11/2002 | Hall |
| 2002/0188207 A1 | 12/2002 | Richter |
| 2003/0010808 A1 | 1/2003 | Uhland et al. |
| 2003/0028094 A1 | 2/2003 | Kumar et al. |
| 2003/0031587 A1 | 2/2003 | Hu et al. |
| 2003/0085799 A1 | 5/2003 | Ghabra et al. |
| 2003/0105388 A1 | 6/2003 | Roy et al. |
| 2003/0125790 A1 | 7/2003 | Fastovsky et al. |
| 2003/0136417 A1 * | 7/2003 | Fonseca et al. .............. 128/899 |
| 2003/0139677 A1 | 7/2003 | Fonseca et al. |
| 2003/0143775 A1 | 7/2003 | Brady |
| 2003/0151400 A1 | 8/2003 | Petrovich et al. |
| 2003/0179708 A1 | 9/2003 | Kamerman et al. |
| 2003/0185330 A1 | 10/2003 | Hessel et al. |
| 2003/0219220 A1 | 11/2003 | Ellis et al. |
| 2004/0003285 A1 | 1/2004 | Whelan et al. |
| 2004/0011650 A1 | 1/2004 | Zenhausern et al. |
| 2004/0017310 A1 | 1/2004 | Vargas-Hurlston et al. |
| 2004/0036626 A1 | 2/2004 | Chan et al. |
| 2004/0057589 A1 | 3/2004 | Pedersen et al. |
| 2004/0059348 A1 | 3/2004 | Geske et al. |
| 2004/0073137 A1 | 4/2004 | Lloyd et al. |
| 2004/0077117 A1 | 4/2004 | Ding et al. |
| 2004/0082851 A1 | 4/2004 | Bilgen et al. |
| 2004/0113790 A1 | 6/2004 | Hamel et al. |
| 2004/0118997 A1 | 6/2004 | Lehmann et al. |
| 2004/0122494 A1 | 6/2004 | Eggers et al. |
| 2004/0157367 A1 | 8/2004 | Wong et al. |
| 2004/0176672 A1 | 9/2004 | Silver et al. |
| 2004/0181206 A1 | 9/2004 | Chiu et al. |
| 2004/0211260 A1 | 10/2004 | Girmonsky et al. |
| 2004/0236209 A1 | 11/2004 | Misic et al. |
| 2005/0043670 A1 | 2/2005 | Rosenberg |
| 2005/0046558 A1 | 3/2005 | Buenz et al. |
| 2005/0075697 A1 | 4/2005 | Olson et al. |
| 2005/0085703 A1 | 4/2005 | Behm |
| 2005/0154321 A1 | 7/2005 | Wolinsky et al. |
| 2005/0187482 A1 | 8/2005 | O'Brien et al. |
| 2005/0194174 A1 | 9/2005 | Hipwell et al. |
| 2005/0229710 A1 | 10/2005 | O'Dowd et al. |
| 2006/0025704 A1 | 2/2006 | Stendel et al. |
| 2006/0047327 A1 | 3/2006 | Colvin et al. |
| 2006/0052737 A1 | 3/2006 | Bertrand et al. |
| 2006/0052782 A1 | 3/2006 | Morgan et al. |
| 2006/0129056 A1 | 6/2006 | Leuthardt et al. |
| 2006/0174712 A1 | 8/2006 | O'Brien et al. |
| 2006/0177956 A1 | 8/2006 | O'Brien et al. |
| 2006/0178586 A1 | 8/2006 | Dobak |
| 2006/0196277 A1 | 9/2006 | Allen et al. |
| 2006/0235310 A1 | 10/2006 | O'Brien et al. |
| 2006/0241354 A1 | 10/2006 | Allen |
| 2006/0244465 A1 | 11/2006 | Kroh et al. |
| 2006/0283007 A1 | 12/2006 | Cros et al. |
| 2006/0287598 A1 | 12/2006 | Lasater et al. |
| 2006/0287602 A1 | 12/2006 | O'Brien et al. |
| 2006/0287700 A1 | 12/2006 | White et al. |
| 2007/0049845 A1 | 3/2007 | Fleischman et al. |
| 2007/0096715 A1 | 5/2007 | Joy et al. |
| 2007/0100215 A1 | 5/2007 | Powers et al. |
| 2007/0107524 A1 | 5/2007 | O'Brien et al. |
| 2007/0118038 A1 | 5/2007 | Bodecker et al. |
| 2007/0181331 A1 | 8/2007 | Kroh et al. |
| 2007/0185546 A1 | 8/2007 | Tseng et al. |
| 2007/0199385 A1 * | 8/2007 | O'Brien et al. .............. 73/718 |
| 2007/0210786 A1 | 9/2007 | Allen et al. |
| 2007/0222603 A1 | 9/2007 | Lai et al. |
| 2007/0236213 A1 | 10/2007 | Paden et al. |
| 2007/0247138 A1 | 10/2007 | Miller et al. |
| 2007/0261497 A1 | 11/2007 | O'Brien et al. |
| 2007/0276294 A1 | 11/2007 | Gupta et al. |
| 2008/0029590 A1 | 2/2008 | Zosimadis et al. |
| 2008/0060834 A1 | 3/2008 | Eck et al. |
| 2008/0060844 A1 | 3/2008 | Teske et al. |
| 2008/0061955 A1 | 3/2008 | Tang et al. |
| 2008/0077016 A1 | 3/2008 | Sparks et al. |

(56) References Cited

U.S. PATENT DOCUMENTS

| | | |
|---|---|---|
| 2008/0078567 A1 | 4/2008 | Miller et al. |
| 2008/0081962 A1 | 4/2008 | Miller et al. |
| 2008/0272733 A1 | 11/2008 | Huang |
| 2009/0030291 A1 | 1/2009 | O'Brien et al. |
| 2009/0030397 A1 | 1/2009 | Stofer et al. |
| 2009/0033486 A1 | 2/2009 | Costantino |
| 2009/0033846 A1 | 2/2009 | Yamada et al. |
| 2009/0224773 A1 | 9/2009 | Joy et al. |
| 2009/0224837 A1 | 9/2009 | Joy et al. |
| 2009/0273353 A1 | 11/2009 | Kroh et al. |
| 2009/0278553 A1 | 11/2009 | Kroh et al. |
| 2010/0022896 A1 | 1/2010 | Yadav et al. |
| 2010/0026318 A1 | 2/2010 | Kroh et al. |
| 2010/0058583 A1 | 3/2010 | Cros et al. |
| 2012/0016228 A1 | 1/2012 | Kroh et al. |
| 2014/0084943 A1 | 3/2014 | Kroh et al. |

FOREIGN PATENT DOCUMENTS

| | | |
|---|---|---|
| AU | 2006262234 A1 | 1/2007 |
| AU | 2009201749 A1 | 5/2009 |
| AU | 2009201750 A1 | 5/2009 |
| AU | 2012247061 A1 | 11/2012 |
| AU | 2013263860 A1 | 1/2014 |
| CA | 1158061 | 6/1983 |
| CA | 2539261 A1 | 3/2005 |
| CA | 2613361 A1 | 1/2007 |
| DE | 3330519 A1 | 3/1985 |
| DE | 19510452 A1 | 10/1995 |
| DE | 19644858.5 | 10/1996 |
| DE | 19853135 A1 | 5/2000 |
| DE | 10052053 A1 | 4/2002 |
| DE | 10135568 A1 | 2/2003 |
| EP | 0072003 A2 | 2/1983 |
| EP | 0450653 A2 | 10/1991 |
| EP | 0337035 | 11/1993 |
| EP | 0646365 | 4/1995 |
| EP | 1491137 A2 | 12/2004 |
| EP | 1677852 A2 | 7/2006 |
| EP | 1817593 A2 | 8/2007 |
| EP | 1893081 A2 | 3/2008 |
| EP | 2265164 A1 | 12/2010 |
| EP | 2268218 A2 | 1/2011 |
| EP | 2456502 A1 | 5/2012 |
| JP | 5870399 | 11/1984 |
| JP | 63171331 | 7/1988 |
| JP | 6481597 | 3/1989 |
| JP | 09259384 | 10/1997 |
| WO | WO 83/03348 | 10/1983 |
| WO | WO 90/06723 | 6/1990 |
| WO | WO-93/08871 A1 | 5/1993 |
| WO | WO 95/33517 | 12/1995 |
| WO | WO 97/09926 | 3/1997 |
| WO | WO-97/11641 A1 | 4/1997 |
| WO | WO 97/32518 | 9/1997 |
| WO | WO 97/32519 | 9/1997 |
| WO | WO 97/33513 | 9/1997 |
| WO | WO-98/47727 A1 | 10/1998 |
| WO | WO 99/34731 | 7/1999 |
| WO | WO 00/16686 | 3/2000 |
| WO | WO 01/00089 | 1/2001 |
| WO | WO-01/35872 A1 | 5/2001 |
| WO | WO 01/87137 | 11/2001 |
| WO | WO 01/97908 | 12/2001 |
| WO | WO-02/058551 A2 | 8/2002 |
| WO | WO-03/032009 A2 | 4/2003 |
| WO | WO 03/061504 | 7/2003 |
| WO | WO-2004/014456 A2 | 2/2004 |
| WO | WO-2004/098701 A1 | 11/2004 |
| WO | WO-2005/019785 A2 | 3/2005 |
| WO | WO-2005/027998 A2 | 3/2005 |
| WO | WO-2006/049796 A2 | 5/2006 |
| WO | WO-2006/086113 A2 | 8/2006 |
| WO | WO-2006/086114 A2 | 8/2006 |
| WO | WO-2006/096582 A1 | 9/2006 |
| WO | WO-2007/002185 A2 | 1/2007 |
| WO | WO-2007/002224 A2 | 1/2007 |
| WO | WO-2007/002225 A2 | 1/2007 |
| WO | WO-2007/008493 A1 | 1/2007 |
| WO | WO-2007/030489 A1 | 3/2007 |
| WO | WO-2007/047571 A2 | 4/2007 |
| WO | WO-2007/047794 A2 | 4/2007 |
| WO | WO-2007/106490 A2 | 9/2007 |
| WO | WO-2008/015679 A2 | 2/2008 |
| WO | WO-2008/031011 A1 | 3/2008 |
| WO | WO-2008/031095 A1 | 3/2008 |
| WO | WO-2008/047727 A1 | 4/2008 |
| WO | WO-2009/146089 A2 | 12/2009 |
| WO | WO-2009/146090 A1 | 12/2009 |
| WO | WO-2011/011104 A1 | 1/2011 |

OTHER PUBLICATIONS

M. Gawenda, J. Heckenkamp, M. Zaehringer, J. Brunkwall; "Intra-Aneurysm Sac Pressure-The Holy Gail of Endoluminal Grafting of AAA"; Eur J Vasc Endovasc Surg, vol. 24, Aug. 2002, pp. 139-145.

GWH Schurink, NJM Arts, J Wild, J.M Van Baalen, Tam Chutner, LJ Schultze Kool, JH Van Bockel; "Endoleakage After Stent-Graft Treatment of Abdominal Aneurysm: Implications on Pressure and Imaging-An In Vitro Study"; Journal of Vascular Surgery, vol. 28, No. 2, pp. 234-241.

B. Sonesson, N. Dias, M. Malina, P. Olofsson, D. Griffin, B. Lindblad, K. Ivancev; "Intra-Aneurysm Pressure Measurements in Successfully Excluded Abdominal Aortic Aneurysm After Endovascular Repair"; Journal of Vascular Surgery, vol. 37, No. 4, Apr. 2003, pp. 733-738.

C.S. Skillern, S.L. Stevens, K.T. Piercy, R.L. Donnell, M.B. Freeman, M.H. Goldman; "Endotension in an Experimental Aneurysm Model"; Journal of Vascular Surgery, vol. 36, No. 4, Oct. 2002, pp. 814-817.

G.D. Treharne, I.M. Loftus, M.M. Thompson, N. Leonard, J. Smith, G. Fishwick, PRF Bell; "Quality Control During Endovascular Aneurysm Repair: Monitoring Aneurysmal Sac Pressure and Superficial Femoral Artery Flow Velocity"; J. Endovasc Surg, 1999, 6, pp. 239-245.

M.L. Manwaring, V.D. Malbasa, K.L. Manwaring: "Remote Monitoring of Intercranial Pressure"; Institute of Concology; Annals of the Academy of Studencia Apr. 2001; pp. 77-80.

GWH Schurink, NJM Arts, J.M Van Baalen, L.J Schultze Kool, JH Van Bockel; "Experimental Study of the Influence of Endoleakage Size on Pressure in the Aneurysm Sac and the Consequences of Thrombosis"; Bristish Journal of Surgery 2002, 87, pp. 71-78.

K. Ouriel; "role of intrasac Pressure Measurements After EVAR: Can They Be Followed Noninvasively?"; Combined Session: Vascular Surgery and Interventional Radiology; VII 4.1.

R.A. Baum, J.P. Carpenter, C. Cope, M.A. Golden, O.C. Velazquez, D.G. Neschis, M.E. Mitchell, C.F. Barker, R.M. Fairman; "Aneurysm Sac Pressure measurements After Endovascular Repair of Abdominal Aortic Aneurysms"; Journal of Vascular Surgery, vol. 33, No. 1, Jan. 2001, pp. 32-41.

P.L. Harris, S. Dimitri; "Predicting failure of endovascular Aneurysm repair"; Eur J Vas Endovasc Surg, vol. 17, Jan. 1999; pp. 1-2.

G. Akingba, A. Cheng, A. Shum, P. Yang; "An Implantable Pressure Sensor for Aneurysmal Disease".

K.F. Adams, Jr.; "Guiding Heart Failure Care by Invasive Hemodynamic Measurements: Possible or Useful?", Journal of cardiac failure, vol. 8, No. 2, Apr. 2002, pp. 71-73.

A. Magalski, P. Adamson, F. Gadler, M. Boehm, D. Steinhaus, D. Reynolds, K. Vlach, C. Linde, Cremers, B. Sparks, T. Bennet; "Continuous Ambulatory Right Heart Presure Measurements with an Implantable Hemodynamic Monitor: A Multicenter, 12-Month Follow-Up Study of Patients with Chronic Heart Failure"; Journal of Cardiac failure, vol. 8, Apr. 2002, pp. 63-70.

R. Shabetai; "Monitoring Heart Failure Hemodynamics with an Implanted Device: Its Potential to Improve Outcome"; Journal of the American College of Cardiology; vol. 41, No. 4, Feb. 19, 2003; pp. 572-573.

(56) References Cited

OTHER PUBLICATIONS

J.C. Parodi, R. Berguer, L.M. Ferreira, R. Lamura, M.L. Schererhorn; "intra-eneurysmal Pressure After Incomplete Endovascular Exclusion"; Journal of Vascular Surgery, vol. 24, No. 5, Nov. 2001, pp. 909-914.
M. Gawenda, J. Heckenkamp, S. Winter, G. Jaschke, J. Brunkwall; Pressure if Transmitted Through PTFE and Dacron Grafts Leading the Aneurysm Sac Pressure Endoluminal Grafting of AAA—An In Vitro Study; Vascular Centre, university of Cologne, Germany.
T. Akin, B. Ziaie, K. Najafi; "RF Telemetry Powering and Controlling of Hermetically Sealed Integrated Sensors and Actuators"; Center for Integrated Sensors and Circuits; Department of Electrical Engineering and Computer Science; University of Michigan; Ann Arbor, Michigan 48109-2122; pp. 145-148.
H.E. Haynes, A.L. Witchey; "Medical electronics: The Pill That Talks"; DEP, Camden, N.J.
A. Dehennis, K.D. Wise; "A Double-Sided Single-Chip Wireless Pressure Sensor": Engineering Research Center for Wireless Integrated Microsystems; Department of Electrical Engineering and Computer Science; The University of Michigan, Ann Arbor, MI 48109-2122 US.
J. Zhe, R.R. Farmer, V. Modi; "A MEMS Device for Measurement of Skin Friction with Capacitive Sensing"; Department of Mechanical Engineering, Columbia university, NY 10027; Microelectronics research Center, New Jersey institute of Technology, Newark, NJ 07102.
T. Chuter, K. Ivancev, M. Malina, T. Resch, J. Brunkwall, B. Lindblad, B. Risberg; "Endovascular and Surgical techniques"; Eur J. Vasc Endovasc Surg vol. 13, Jan. 1997, pp. 85-87.
J.T. Farrar, C. Berkley, V.K. Zworykin; " Telemetering of Intraenteric pressure in man by an Externally Energized Wireless Capsule"; Science, New Series, vol. 131, Issue 3416 (Jun. 17, 1960), 1814.
Collins, Miniature Passive Pressure Transensor for Implanting in the Eye, IEEE Transactions on Bio-Medical Engineering, vol. BME-14, No. 2, Apr. 1967.
George et al., Ceramic Windows to the Future, http://matse1.mse.uiuc.edu/ceramics/ceramics.html, 1995, p. 4.
U.S. Appl. No. 13/850,022, Yadav.
"Helix," The American Heritage Dictionary of the English Language. Boston, MA: Houghton Mifflin. Http://www.credoreference.com/entry/7055911 Aug. 21, 2008.
"Interfere," The American Heritage Dictionary of the English Language. Boston, MA: Houghton Mifflin. Http://www.credoreference.com/entry/7072413 Aug. 22, 2008.
"Spiral," The American Heritage Dictionary of the English Language. Boston, MA: Houghton Mifflin. Http://www.credoreference.com/entry/7129585 Aug. 21, 2008.
Akar O, et al. "A Wireless Batch Sealed Absolute Capacitive Pressure Sensor," Sensor and Actuators. Dec. 15, 2001, 95(1), pp. 29-38.
Allen, "Micromachined endovascularly implantable wireless aneurysm pressue sensors," International Conference on Solid State Sensors, Actuators and Microsystems, No. 13, pp. 275-278 (2005).
Chirlian, "Basic network theory," McGraw Hill Book Co., Impendance section: pp. 275-283, 350-355 (1969).
Fonseca, "High temperature characterization of ceramic pressure sensors," vol. 1, pp. 486-489 (2001).
Harpster, "A passive wireless integrated humidity sensor," Micro Electro Mechanical Systems, vol. IEEEMEMSCONF, No. 14, pp. 553-557 (2001).
Puers, et al. "Electrodeposited copper indicators for intraocular pressure telemetry; electrodeposited copper inductors for IOP telemetry," Journal of Micromechanics & Microengineering, vol. 10(2), pp. 124-129 (2000).
Seifert, et al. "Wirelessly interrogable acoustic sensors," Frequency and Time Form, (Online) No. 4, pp. 1013-1018 (1999).
Notice of Allowance issued Aug. 5, 2011 for U.S. Appl. No. 12/416,904, filed Apr. 1, 2009 and issued as U.S. Pat. No. 8,026,729 on Sep. 27, 2011 (Inventor—Kroh; Applicant—CardioMEMS) (pp. 1-9).
Issue Notification issued Sep. 27, 2011 for U.S. Appl. No. 12/416,904, filed Apr. 1, 2009 and issued as U.S. Pat. No. 8,026,729 on Sep. 27, 2011 (Inventor—Kroh; Applicant—CardioMEMS) (pp. 1-1).
Non-Final Office Action issued Mar. 14, 2014 for U.S. Appl. No. 13/245,553, filed Sep. 26, 2011 and published as U.S. 2012/0016228 on Jan. 19, 2012 (Inventor—Kroh; Applicant—CardioMEMS) (pp. 1-12).
Supplemental European Search Report issued Apr. 11, 2013 for European Patent Application No. 09755451.3, which was filed on Apr. 1, 2009 and published as EP 2268218 on Jan. 5, 2011 (Inventor—Kroh; Applicant—CardioMEMS) (pp. 1-5).
International Search Report and Written Opinion issued Nov. 17, 2009 for International Patent Application No. PCT/US2009/039220, which was filed on Apr. 1, 2009 and published as WO 2009/146089 on Dec. 3, 2009 (Inventor—Kroh; Applicant—CardioMEMS) (pp. 1-10).
International Preliminary Report on Patentability issued Oct. 5, 2010 for International Patent Applicantion No. PCT/US2009/039220, which was filed on Apr. 1, 2009 and published as WO 2009/146089 on Dec. 3, 2009 (Inventor—Kroh; Applicant—CardioMEMS) (pp. 1-6).
Restriction Requirement issued Oct. 12, 2011 for U.S. Appl. No. 12/416,916, filed Apr. 1, 2009 and issued as U.S. Pat. No. 8,278,941 on Oct. 2, 2012 (Inventor—Kroh; Applicant—CardioMEMS) (pp. 1-6).
Response to Restriction Requirement filed Oct. 28, 2011 for U.S. Appl. No. 12/416,916, filed Apr. 1, 2009 and issued as U.S. Pat. No. 8,278,941 on Oct. 2, 2012 (Inventor—Kroh; Applicant—CardioMEMS) (pp. 1-3).
Ex Parte Quayle Action issued Mar. 15, 2012 for U.S. Appl. No. 12/416,916, filed Apr. 1, 2009 and issued as U.S. Pat. No. 8,278,941 on Oct. 2, 2012 (Inventor—Kroh; Applicant—CardioMEMS) (pp. 1-5).
Response to Ex Parte Quayle Communication filed May 15, 2012 for U.S. Appl. No. 12/416,916, filed Apr. 1, 2009 and issued as U.S. Pat. No. 8,278,941 on Oct. 2, 2012 (Inventor—Kroh; Applicant—CardioMEMS) (pp. 1-9).
Notice of Allowance issued May 25, 2012 for U.S. Appl. No. 12/416,916, filed Apr. 1, 2009 and issued as U.S. Pat. No. 8,278,941 on Oct. 2, 2012 (Inventor—Kroh; Applicant—CardioMEMS) (pp. 1-8).
Issue Notification issued Oct. 2, 2012 for U.S. Appl. No. 12/416,916, filed Apr. 1, 2009 and issued as U.S. Pat. No. 8,278,941 on Oct. 2, 2012 (Inventor—Kroh; Applicant—CardioMEMS) (pp. 1-1).
Supplemental European Search Report issued Sep. 2, 2013 for European Patent Application No. 09755452.1, which was filed on Apr. 1, 2009 and published as EP 2265164 on Dec. 29, 2010 (Inventor—Kroh; Application—CardioMEMS) (pp. 1-7).
International Search Report and Written Opinion issued Nov. 12, 2009 for International Patent Application No. PCT/US2009/039222, which was filed on Apr. 1, 2009 and published as WO 2009/146090 on Dec. 3, 2009 (Inventor—Kroh; Applicant—CardioMEMS) (pp. 1-5).
International Preliminary Report on Patentability issued Oct. 5, 2010 for International Patent Application No. PCT/US2009/039222, which was filed on Apr. 1, 2009 and published as WO 2009/146090 on Dec. 3, 2009 (Inventor—Kroh; Applicant—CardioMEMS) (pp. 1-4).
Supplemental European Search Report issued Apr. 29, 2013 for European Patent Application No. 10802580.0, which was filed on May 3, 2010 and published as EP 2456502 on May 30, 2012 (Inventor—Yadev; Applicant—CardioMEMS) (pp. 1-11).
International Search Report and Written Opinion issued Jan. 7, 2011 for International Patent Application No. PCT/US2010/033396, which was filed on May 3, 2010 and published as WO 2011/011104 on Jan. 27, 2011 (Inventor—Yadev; Applicant—CardioMEMS) (pp. 1-7).
International Preliminary Report on Patentability issued Jan. 24, 2012 for International Patent Application No. PCT/US2010/033396, which was filed on May 3, 2010 and published as WO 2011/011104 on Jan. 27, 2011 (Inventor—Yadev; Applicant—CardioMEMS) (pp. 1-5).

(56) References Cited

OTHER PUBLICATIONS

Preliminary Amendment filed Nov. 4, 2009 for U.S. Appl. No. 12/612,070, filed Nov. 4, 2009 and published as U.S. 2010/0058583 on Mar. 11, 2010 (Inventor—Cros; Applicant—CardioMEMS) (pp. 1-3).
Restriction Requirement issued Dec. 9, 2010 for U.S. Appl. No. 12/612,070, filed Nov. 4, 2009 and published as U.S. 2010/0058583 on Mar. 11, 2010 (Inventor—Cros; Applicant—CardioMEMS) (pp. 1-6).
Preliminary Amendment and Response to Restriction Requirement filed Jun. 9, 2011 for U.S. Appl. No. 12/612,070, filed Nov. 4, 2009 and published as U.S. 2010/0058583 on Mar. 11, 2010 (Inventor—Cros; Applicant—CardioMEMS) (pp. 1-4).
Non-Final Office Action issued Aug. 26, 2011 for U.S. Appl. No. 12/612,070, filed Nov. 4, 2009 and published as U.S. 2010/0058583 on Mar. 11, 2010 (Inventor—Cros; Applicant—CardioMEMS) (pp. 1-8).
Response to Non-Final Office Action filed Jan. 31, 2012 for U.S. Appl. No. 12/612,070, filed Nov. 4, 2009 and published as U.S. 2010/0058583 on Mar. 11, 2010 (Inventor—Cros; Applicant—CardioMEMS) (pp. 1-13).
Response to Final Office Action filed Jun. 26, 2012 for U.S. Appl. No. 12/612,070, filed Nov. 4, 2009 and published as U.S. 2010/0058583 on Mar. 11, 2010 (Inventor—Cros; Applicant—CardioMEMS) (pp. 1-8).
Non-Final Office Action issued Jul. 18, 2013 for U.S. Appl. No. 12/612,070, filed Nov. 4, 2009 and published as U.S. 2010/0058583 on Mar. 11, 2010 (Inventor—Cros; Applicant—CardioMEMS) (pp. 1-7).
Non-Final Office Action issued Feb. 24, 2014 for U.S. Appl. No. 12/612,070, filed Nov. 4, 2009 and published as U.S. 2010/0058583 on Mar. 11, 2010 (Inventor—Cros; Applicant—CardioMEMS) (pp. 1-10).
Restriction Requirement issued Jan. 15, 2008 for U.S. Appl. No. 11/204,812, filed Aug. 16, 2005 and issued as U.S. Pat. No. 7,621,036 on Nov. 24, 2009 (Inventor—Cros; Applicant—CardioMEMS) (pp. 1-7).
Response to Restriction Requirement filed Feb. 15, 2008 for U.S. Appl. No. 11/204,812, filed Aug. 16, 2005 and issued as U.S. Pat. No. 7,621,036 on Nov. 24, 2009 (Inventor—Cros; Applicant—CardioMEMS) (pp. 1-5).
Restriction Requirement issued Apr. 11, 2008 for U.S. Appl. No. 11/204,812, filed Aug. 16, 2005 and issued as U.S. Pat. No. 7,621,036 on Nov. 24, 2009 (Inventor—Cros; Applicant—CardioMEMS) (pp. 1-7).
Response to Restriction Requirement filed May 12, 2008 for U.S. Appl. No. 11/204,812, filed Aug. 16, 2005 and issued as U.S. Pat. No. 7,621,036 on Nov. 24, 2009 (Inventor—Cros; Applicant—CardioMEMS) (pp. 1-5).
Non-Final Office Action issued Jun. 12, 2008 for U.S. Appl. No. 11/204,812, filed Aug. 16, 2005 and issued as U.S. Pat. No. 7,621,036 on Nov. 24, 2009 (Inventor—Cros; Applicant—CardioMEMS) (pp. 1-7).
Response to Non-Final Office Action filed Dec. 12, 2008 for U.S. Appl. No. 11/204,812, filed Aug. 16, 2005 and issued as U.S. Pat. No. 7,621,036 on Nov. 24, 2009 (Inventor—Cros; Applicant—CardioMEMS) (pp. 1-15).
Examiner Interview Summary issued Apr. 16, 2009 for U.S. Appl. No. 11/204,812, filed Aug. 16, 2005 and issued as U.S. Pat. No. 7,621,036 on Nov. 24, 2009 (Inventor—Cros; Applicant—CardioMEMS) (pp. 1-2).
Notice of Allowance issued Jul. 10, 2009 for U.S. Appl. No. 11/204,812, filed Aug. 16, 2005 and issued as U.S. Pat. No. 7,621,036 on Nov. 24, 2009 (Inventor—Cros; Applicant—CardioMEMS) (pp. 1-4).
Notice of Allowance issued Sep. 29, 2009 for U.S. Appl. No. 11/204,812, filed Aug. 16, 2005 and issued as U.S. Pat. No. 7,621,036 on Nov. 24, 2009 (Inventor—Cros; Applicant—CardioMEMS) (pp. 1-2).

Examiner Interview Summary issued Oct. 30, 2009 for U.S. Appl. No. 11/204,812, filed Aug. 16, 2005 and issued as U.S. Pat. No. 7,621,036 on Nov. 24, 2009 (Inventor—Cros; Applicant—CardioMEMS) (pp. 1-3).
Issue Notification issued Nov. 24, 2009 for U.S. Appl. No. 11/204,812, filed Aug. 16, 2005 and issued as U.S. Pat. No. 7,621,036 on Nov. 24, 2009 (Inventor—Cros; Applicant—CardioMEMS) (pp. 1-1).
Preliminary Amendment filed Jun. 21, 2006 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-8).
Non-Final Office Action issued Oct. 29, 2007 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-12).
Supplemental Response to Non-Final Office Action filed May 30, 2008 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-19).
Restriction Requirement issued Aug. 22, 2008 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-6).
Final Office Action issued Aug. 25, 2008 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-12).
Response and Amendment to Final Office Action filed Feb. 25, 2009 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-14).
Non-Final Office Action issued Jun. 1, 2009 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-11).
Amendment and Response to Non-Final Office Action filed Oct. 23, 2009 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-11).
Final Office Action issued Jul. 29, 2010 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-12).
Amendment in Response to Final Office Action filed Jan. 31, 2011 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-11).
Non-Final Office Action issued Jan. 16, 2014 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-1 1).
International Preliminary Report on Patentability issued Dec. 24, 2007 for International Patent Applicantion No. PCT/US2006/024185, which was filed on Jun. 21, 2006 and published as WO 2007/002225 on Jan. 4, 2007 (Inventor—O'Brien; Applicant—CardioMEMS) (pp. 1-7).
International Search Report and Written Opinion issued Jan. 25, 2007 for International Patent Applicantion No. PCT/US2006/024185, which was filed on Jun. 21, 2006 and published as WO 2007/002225 on Jan. 4, 2007 (Inventor—O'Brien; Applicant—CardioMEMS) (pp. 1-11).
Supplemental European Search Report issued May 27, 2009 for European Patent Application No. 4078884.1, which was filed on Sep. 16, 2004 and published as EP 1677852 on Jul. 12, 2006 (Inventor—O'Brien; Applicant—CardioMEMS) (pp. 1-5).
International Preliminary Report on Patentability issued Oct. 3, 2006 for International Patent Application No. PCT/US2004/030727, which was filed on Sep. 16, 2004 and published as WO 2005/027998 on Mar. 31, 2005 (Inventor—O'Brien; Applicant—CardioMEMS) (pp. 1-9).
International Search Report and Written Opinoin issued Aug. 4, 2006 for International Patent Application No. PCT/US2004/030727,

(56) References Cited

OTHER PUBLICATIONS which was filed on Sep. 16, 2004 and published as WO 2005/027998 on Mar. 31, 2005 (Inventor—O'Brien; Applicant—CardioMEMS) (pp. 1-12).
Restriction Requirement issued Jul. 28, 2006 for U.S. App. No. 11/105,294, filed Apr. 13, 2005 and issued as U.S. Pat. No. 7,245,117 on Jul. 17, 2007 (Inventor—Joy; Applicant—CardioMEMS) (pp. 1-7).
Response to Restriction Requirement filed Aug. 28, 2006 for U.S. Appl. No. 11/105,294, filed Apr. 13, 2005 and issued as U.S. Pat. No. 7,245,117 on Jul. 17, 2007 (Inventor—Joy; Applicant—CardioMEMS) (pp. 1-3).
Examiner Interview Summary issued Sep. 20, 2006 for U.S. Appl. No. 11/105,294, filed Apr. 13, 2005 and issued as U.S. Pat. No. 7,245,117 on Jul. 17, 2007 (Inventor—Joy; Applicant—CardioMEMS) (pp. 1-1).
Notice of Allowance issued Sep. 20, 2006 for U.S. Appl. No. 11/105,294, filed Apr. 13, 2005 and issued as U.S. Pat. No. 7,245,117 on Jul. 17, 2007 (Inventor—Joy; Applicant—CardioMEMS) (pp. 1-6).
Notice of Allowance issued Nov. 6, 2006 for U.S. Appl. No. 11/105,294, filed Apr. 13, 2005 and issued as U.S. Pat. No. 7,245,117 on Jul. 17, 2007 (Inventor—Joy; Applicant—CardioMEMS) (pp. 1-2).
Issue Notification issued Jun. 27, 2007 for U.S. Appl. No. 11/105,294, filed Apr. 13, 2005 and issued as U.S. Pat. No. 7,245,117 on Jul. 17, 2007 (Inventor—Joy; Applicant—CardioMEMS) (pp. 1-1).
Restriction Requirement issued Jan. 22, 2007 for U.S. Appl. No. 11/479,527, filed Jun. 30, 2006 and issued as U.S. Pat. No. 7,432,723 on Oct. 7, 2008 (Inventor—Ellis; Applicant—CardioMEMS) (pp. 1-5).
Response to Restriction Requirement filed Feb. 16, 2007 for U.S. Appl. No. 11/479,527, filed Jun. 30, 2006 and issued as U.S. Pat. No. 7,432,723 on Oct. 7, 2008 (Inventor—Ellis; Applicant—CardioMEMS) (pp. 1-6).
Non-Final Office Action issued Mar. 29, 2007 for U.S. Appl. No. 11/479,527, filed Jun. 30, 2006 and issued as U.S. Pat. No. 7,432,723 on Oct. 7, 2008 (Inventor—Ellis; Applicant—CardioMEMS) (pp. 1-8).
Examiner Interview Summary issued Jun. 26, 2007 for U.S. Appl. No. 11/479,527, filed Jun. 30, 2006 and issued as U.S. Pat. No. 7,432,723 on Oct. 7, 2008 (Inventor—Ellis; Applicant—CardioMEMS) (pp. 1-3).
Amendment and Response filed Jul. 26, 2007 for U.S. Appl. No. 11/479,527, filed Jun. 30, 2006 and issued as U.S. Pat. No. 7,432,723 on Oct. 7, 2008 (Inventor—Ellis; Applicant—CardioMEMS) (pp. 1-12).
Notice of Allowance issued Mar. 27, 2008 for U.S. Appl. No. 11/479,527, filed Jun. 30, 2006 and issued as U.S. Pat. No. 7,432,723 on Oct. 7, 2008 (Inventor—Ellis; Applicant—CardioMEMS) (pp. 1-9).
Notice of Allowance issued May 23, 2008 for U.S. Appl. No. 11/479,527, filed Jun. 30, 2006 and issued as U.S. Pat. No. 7,432,723 on Oct. 7, 2008 (Inventor—Ellis; Applicant—CardioMEMS) (pp. 1-6).
Notice of Allowance issued Aug. 12, 2008 for U.S. Appl. No. 11/479,527, filed Jun. 30, 2006 and issued as U.S. Pat. No. 7,432,723 on Oct. 7, 2008 (Inventor—Ellis; Applicant—CardioMEMS) (pp. 1-2).
Issue Notification issued Oct. 7, 2008 for U.S. Appl. No. 11/479,527, filed Jun. 30, 2006 and issued as U.S. Pat. No. 7,432,723 on Oct. 7, 2008 (Inventor—Ellis; Applicant—CardioMEMS) (pp. 1-1).
Notice of Allowance issued Aug. 17, 2007 for U.S. Appl. No. 11/748,053, filed May 14, 2007 and issued as U.S. Pat. No. 7,439,723 on Oct. 21, 2008 (Inventor—Allen; Applicant—CardioMEMS) (pp. 1-8).
Notice of Allowance issued Jan. 2, 2008 for U.S. Appl. No. 11/748,053, filed May 14, 2007 and issued as U.S. Pat. No. 7,439,723 on Oct. 21, 2008 (Inventor—Allen; Applicant—CardioMEMS) (pp. 1-6).
Notice of Allowance issued May 8, 2008 for U.S. Appl. No. 11/748,053, filed May 14, 2007 and issued as U.S. Pat. No. 7,439,723 on Oct. 21, 2008 (Inventor—Allen; Applicant—CardioMEMS) (pp. 1-6).
Notice of Allowance issued Aug. 15, 2008 for U.S. Appl. No. 11/748,053, filed May 14, 2007 and issued as U.S. Pat. No. 7,439,723 on Oct. 21, 2008 (Inventor—Allen; Applicant—CardioMEMS) (pp. 1-6).
Issue Notification issued Oct. 21, 2008 for U.S. Appl. No. 11/748,053, filed May 14, 2007 and issued as U.S. Pat. No. 7,439,723 on Oct. 21, 2008 (Inventor—Allen; Applicant—CardioMEMS) (pp. 1-1).
Notice of Allowance issued Oct. 2, 2007 for U.S. Appl. No. 11/717,967, filed Mar. 14, 2007 and issued as U.S. Pat. No. 7,466,120 on Dec. 16, 2008 (Inventor—Miller; Applicant—CardioMEMS) (pp. 1-7).
Notice of Allowance issued Nov. 21, 2007 for U.S. Appl. No. 11/717,967, filed Mar. 14, 2007 and issued as U.S. Pat. No. 7,466,120 on Dec. 16, 2008 (Inventor—Miller; Applicant—CardioMEMS) (pp. 1-2).
Notice of Allowance issued Mar. 31, 2008 for U.S. Appl. No. 11/717,967, filed Mar. 14, 2007 and issued as U.S. Pat. No. 7,466,120 on Dec. 16, 2008 (Inventor—Miller; Applicant—CardioMEMS) (pp. 1-6).
Notice of Allowance issued Jul. 14, 2008 for U.S. Appl. No. 11/717,967, filed Mar. 14, 2007 and issued as U.S. Pat. No. 7,466,120 on Dec. 16, 2008 (Inventor—Miller; Applicant—CardioMEMS) (pp. 1-6).
Issue Notification issued Nov. 25, 2008 for U.S. Appl. No. 11/717,967, filed Mar. 14, 2007 and issued as U.S. Pat. No. 7,466,120 on Dec. 16, 2008 (Inventor—Miller; Applicant—CardioMEMS) (pp. 1-1).
Requirement for Restriction issued Sep. 12, 2008 for U.S. Appl. No. 11/613,645, filed Dec. 20, 2006 and issued as U.S. Pat. No. 7,550,978 on Jun. 23, 2009 (Inventor—Kroh; Applicant—CardioMEMS) (pp. 1-5).
Examiner Interview Summary issued Sep. 12, 2008 for U.S. Appl. No. 11/613,645, filed Dec. 20, 2006 and issued as U.S. Pat. No. 7,550,978 on Jun. 23, 2009 (Inventor—Kroh; Applicant—CardioMEMS) (pp. 1-2).
Response to Restriction Requirement filed Oct. 14, 2008 for U.S. Appl. No. 11/613,645, filed Dec. 20, 2006 and issued as U.S. Pat. No. 7,550,978 on Jun. 23, 2009 (Inventor—Kroh; Applicant—CardioMEMS) (pp. 1-6).
Notice of Allowance issued Dec. 16, 2008 for U.S. Appl. No. 11/613,645, filed Dec. 20, 2006 and issued as U.S. Pat. No. 7,550,978 on Jun. 23, 2009 (Inventor—Kroh; Applicant—CardioMEMS) (pp. 1-8).
Notice of Allowance issued Feb. 17, 2009 for U.S. Appl. No. 11/613,645, filed Dec. 20, 2006 and issued as U.S. Pat. No. 7,550,978 on Jun. 23, 2009 (Inventor—Kroh; Applicant—CardioMEMS) (pp. 1-6).
Issue Notification issued Jun. 23, 2009 for U.S. Appl. No. 11/613,645, filed Dec. 20, 2006 and issued as U.S. Pat. No. 7,550,978 on Jun. 23, 2009 (Inventor—Kroh; Applicant—CardioMEMS) (pp. 1-1).
Non-Final Office Action issued Sep. 8, 2006 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-7).
Response to Non-Final Office Action filed Nov. 8, 2006 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-6).
Final Office Action issued Jan. 25, 2007 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-8).

(56) References Cited

OTHER PUBLICATIONS

Response to Final Office Action filed Mar. 19, 2007 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-7).
Advisory Action issued Apr. 16, 2007 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-3).
Pre-Appeal Brief Request for Review filed Apr. 25, 2007 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-6).
Pre-Appeal Brief Conference Decision issued Jul. 2, 2007 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-2).
Response to Final Office Action filed Jan. 25, 2007 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-19).
Non-Final Office Action issued Sep. 20, 2007 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-8).
Response to Non-Final Office Action filed Dec. 7, 2007 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-9).
Final Office Action issued Mar. 21, 2008 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-9).
Response to Final Office Action filed May 8, 2008 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-9).
Advisory Action issued May 30, 2008 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-3).
Non-Final Office Action issued Aug. 6, 2008 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-8).
Response to Non-Final Office Action filed Sep. 24, 2008 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-19).
Final Office Action issued Dec. 17, 2008 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-10).
Response to Final Office Action filed Feb. 17, 2009 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-11).
Advisory Action issued Mar. 9, 2009 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-3).
Non-Final Office Action issued Apr. 14, 2009 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-10).
Response to Non-Final Office Action filed May 18, 2009 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-12).
Notice of Allowance issued Jun. 9, 2009 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-4).
Issue Notification issued Aug. 11, 2009 for U.S. Appl. No. 10/348,894, filed Jan. 23, 2003 and issued as U.S. Pat. No. 7,574,492 on Aug. 11, 2009 (Inventor—Karaoguz; Applicant—CardioMEMS) (pp. 1-1).
Non-Final Office Action issued Jun. 12, 2008 for U.S. Appl. No. 11/668,601, filed Jan. 30, 2007 and issued as U.S. Pat. No. 7,595,647 on Sep. 29, 2009 (Inventor—Kroh; Applicant—CardioMEMS) (pp. 1-9).
Amendment and Response to Non-Final Office Action filed Oct. 13, 2008 for U.S. Appl. No. 11/668,601, filed Jan. 30, 2007 and issued as U.S. Pat. No. 7,595,647 on Sep. 29, 2009 (Inventor—Kroh; Applicant—CardioMEMS) (pp. 112).
Final Office Action issued Jan. 6, 2009 for U.S. Appl. No. 11/668,601, filed Jan. 30, 2007 and issued as U.S. Pat. No. 7,595,647 on Sep. 29, 2009 (Inventor—Kroh; Applicant—CardioMEMS) (pp. 1-13).
Amendment and Response to Final Office Action May 1, 2009 for U.S. Appl. No. 11/668,601, filed Jan. 30, 2007 and issued as U.S. Pat. No. 7,595,647 on Sep. 29, 2009 (Inventor—Kroh; Applicant—CardioMEMS) (pp. 1-9).
Notice of Allowance issued Jun. 1, 2009 for U.S. Appl. No. 11/668,601, filed Jan. 30, 2007 and issued as U.S. Pat. No. 7,595,647 on Sep. 29, 2009 (Inventor—Kroh; Applicant—CardioMEMS) (pp. 1-7).
Issue Notification issued Sep. 9, 2009 for U.S. Appl. No. 11/668,601, filed Jan. 30, 2007 and issued as U.S. Pat. No. 7,595,647 on Sep. 29, 2009 (Inventor—Kroh; Applicant—CardioMEMS) (pp. 1-1).
Non-Final Office Action issued Jun. 24, 2009 for U.S. Appl. No. 12/349,606, filed Jan. 7, 2009 and issued as U.S. Pat. No. 7,679,355 on Mar. 16, 2010 (Inventor—Allen; Applicant—CardioMEMS) (pp. 1-7).
Examiner Interview Summary issued Aug. 25, 2009 for U.S. Appl. No. 12/349,606, filed Jan. 7, 2009 and issued as U.S. Pat. No. 7,679,355 on Mar. 16, 2010 (Inventor—Allen; Applicant—CardioMEMS) (pp. 1-2).
Amendment and Response for Non-Final Office Action filed Sep. 24, 2009 for U.S. Appl. No. 12/349,606, filed Jan. 7, 2009 and issued as U.S. Pat. No. 7,679,355 on Mar. 16, 2010 (Inventor—Allen; Applicant—CardioMEMS) (pp. 19).
Notice of Allowance issued Dec. 15, 2009 for U.S. Appl. No. 12/349,606, filed Jan. 7, 2009 and issued as U.S. Pat. No. 7,679,355 on Mar. 16, 2010 (Inventor—Allen; Applicant—CardioMEMS) (pp. 1-4).
Notice of Allowance issued Feb. 4, 2010 for U.S. Appl. No. 12/349,606, filed Jan. 7, 2009 and issued as U.S. Pat. No. 7,679,355 on Mar. 16, 2010 (Inventor—Allen; Applicant—CardioMEMS) (pp. 1-2).
Issue Notification issued Feb. 24, 2010 for U.S. Appl. No. 12/349,606, filed Jan. 7, 2009 and issued as U.S. Pat. No. 7,679,355 on Mar. 16, 2010 (Inventor—Allen; Applicant—CardioMEMS) (pp. 1-1).
Non-Final Office Action issued Mar. 24, 2010 for U.S. Appl. No. 12/466,541, filed May 15, 2009 and issued as U.S. Pat. No. 7,839,153 on Nov. 23, 2010 (Inventor—Joy; Applicant—CardioMEMS) (pp. 1-8).
Examiner Interview Summary issued Jun. 21, 2010 for U.S. Appl. No. 12/466,541, filed May 15, 2009 and issued as U.S. Pat. No. 7,839,153 on Nov. 23, 2010 (Inventor—Joy; Applicant—CardioMEMS) (pp. 1-4).
Amendment and Response for Non-Final Office Action filed Jun. 24, 2010 for U.S. Appl. No. 12/466,541, filed May 15, 2009 and issued as U.S. Pat. No. 7,839,153 on Nov. 23, 2010 (Inventor—Joy; Applicant—CardioMEMS) (pp. 1-10).
Terminal Disclaimer filed Jun. 24, 2010 for U.S. Appl. No. 12/466,541, filed May 15, 2009 and issued as U.S. Pat. No. 7,839,153 on Nov. 23, 2010 (Inventor—Joy; Applicant—CardioMEMS) (pp. 1-1).
Terminal Disclaimer Review Decision issued Jul. 6, 2010 for U.S. Appl. No. 12/466,541, filed May 15, 2009 and issued as U.S. Pat. No. 7,839,153 on Nov. 23, 2010 (Inventor—Joy; Applicant—CardioMEMS) (pp. 1-1).

(56) References Cited

OTHER PUBLICATIONS

Notice of Allowance issued Aug. 25, 2010 for U.S. Appl. No. 12/466,541, filed May 15, 2009 and issued as U.S. Pat. No. 7,839,153 on Nov. 23, 2010 (Inventor—Joy; Applicant—CardioMEMS) (pp. 1-6).

Issue Notification issued Nov. 3, 2010 for U.S. Appl. No. 12/466,541, filed May 15, 2009 and issued as U.S. Pat. No. 7,839,153 on Nov. 23, 2010 (Inventor—Joy; Applicant—CardioMEMS) (pp. 1-1).

Non-Final Office Action issued Oct. 15, 2010 for U.S. Appl. No. 12/466,595, filed May 15, 2009 and issued as U.S. Pat. No. 7,932,732 on Apr. 26, 2011 (Inventor—Kroh; Applicant—CardioMEMS) (pp. 1-6).

Amendment and Response for Non-Final Office Action filed Dec. 10, 2010 for U.S. Appl. No. 12/466,595, filed May 15, 2009 and issued as U.S. Pat. No. 7,932,732 on Apr. 26, 2011 (Inventor—Kroh; Applicant—CardioMEMS) (pp. 18).

Notice of Allowance issued Dec. 29, 2010 for U.S. Appl. No. 12/466,595, filed May 15, 2009 and issued as U.S. Pat. No. 7,932,732 on Apr. 26, 2011 (Inventor—Kroh; Applicant—CardioMEMS) (pp. 1-4).

Issue Notification issued Apr. 6, 2011 for U.S. Appl. No. 12/466,595, filed May 15, 2009 and issued as U.S. Pat. No. 7,932,732 on Apr. 26, 2011 (Inventor—Kroh; Applicant—CardioMEMS) (pp. 1-1).

Preliminary Amendment filed Oct. 16, 2009 for U.S. Appl. No. 12/545,166, filed Aug. 21, 2009 and issued as U.S. Pat. No. 7,936,174 on May 3, 2011 (Inventor—Kroh; Applicant—CardioMEMS) (pp. 1-3).

Non-Final Office Action issued Jun. 25, 2010 for U.S. Appl. No. 12/545,166, filed Aug. 21, 2009 and issued as U.S. Pat. No. 7,936,174 on May 3, 2011 (Inventor—Kroh; Applicant—CardioMEMS) (pp. 1-7).

Terminal Disclaimer filed Oct. 7, 2010 for U.S. Appl. No. 12/545,166, filed Aug. 21, 2009 and issued as U.S. Pat. No. 7,936,174 on May 3, 2011 (Inventor—Kroh; Applicant—CardioMEMS) (pp. 1-2).

Response to Non-Final Office Action filed Oct. 7, 2010 for U.S. Appl. No. 12/545,166, filed Aug. 21, 2009 and issued as U.S. Pat. No. 7,936,174 on May 3, 2011 (Inventor—Kroh; Applicant—CardioMEMS) (pp. 1-7).

Examiner Interview Summary issued Oct. 12, 2010 for U.S. Appl. No. 12/545,166, filed Aug. 21, 2009 and issued as U.S. Pat. No. 7,936,174 on May 3, 2011 (Inventor—Kroh; Applicant—CardioMEMS) (pp. 1-4).

Terminal Disclaimer Review Decision issued Oct. 31, 2010 for U.S. Appl. No. 12/545,166, filed Aug. 21, 2009 and issued as U.S. Pat. No. 7,936,174 on May 3, 2011 (Inventor—Kroh; Applicant—CardioMEMS) (pp. 1-1).

Notice of Allowance issued Dec. 23, 2010 for U.S. Appl. No. 12/545,166, filed Aug. 21, 2009 and issued as U.S. Pat. No. 7,936,174 on May 3, 2011 (Inventor—Kroh; Applicant—CardioMEMS) (pp. 1-7).

Issue Notification issued Apr. 13, 2011 for U.S. Appl. No. 12/545,166, filed Aug. 21, 2009 and issued as U.S. Pat. No. 7,936,174 on May 3, 2011 (Inventor—Kroh; Applicant—CardioMEMS) (pp. 1-1).

Notice of Allowance issued Mar. 18, 2011 for U.S. Appl. No. 12/765,970, filed Apr. 23, 2010 and issued as U.S. Pat. No. 7,973,540 on Jul. 5, 2011 (Inventor—Kroh; Applicant—CardioMEMS) (pp. 1-8).

Amendment After Notice of Allowance May 24, 2011 for U.S. Appl. No. 12/765,970, filed Apr. 23, 2010 and issued as U.S. Pat. No. 7,973,540 on Jul. 5, 2011 (Inventor—Kroh; Applicant—CardioMEMS) (pp. 1-5).

Issue Notification issued Jun. 15, 2011 for U.S. Appl. No. 12/765,970, filed Apr. 23, 2010 and issued as U.S. Pat. No. 7,973,540 on Jul. 5, 2011 (Inventor—Kroh; Applicant—CardioMEMS) (pp. 1-1).

Non-Final Office Action issued Dec. 8, 2011 for U.S. Appl. No. 13/078,091, filed Apr. 1, 2011 and issued as U.S. Pat. No. 8,237,451 on Aug. 7, 2012 (Inventor—Joy; Applicant—CardioMEMS) (pp. 1-7).

Applicant-Initiated Interview Summary issued Mar. 6, 2012 for U.S. Appl. No. 13/078,091, filed Apr. 1, 2011 and issued as U.S. Pat. No. 8,237,451 on Aug. 7, 2012 (Inventor—Joy; Applicant—CardioMEMS) (pp. 1-3).

Response to Non-Final Office Action issued Mar. 8, 2012 for U.S. Appl. No. 13/078,091, filed Apr. 1, 2011 and issued as U.S. Pat. No. 8,237,451 on Aug. 7, 2012 (Inventor—Joy; Applicant—CardioMEMS) (pp. 1-10).

Notice of Allowance issued Apr. 4, 2012 for U.S. Appl. No. 13/078,091, filed Apr. 1, 2011 and issued as U.S. Pat. No. 8,237,451 on Aug. 7, 2012 (Inventor—Joy; Applicant—CardioMEMS) (pp. 1-7).

Notice of Allowance issued May 17, 2012 for U.S. Appl. No. 13/078,091, filed Apr. 1, 2011 and issued as U.S. Pat. No. 8,237,451 on Aug. 7, 2012 (Inventor—Joy; Applicant—CardioMEMS) (pp. 1-2).

Issue Notification issued Jul. 18, 2012 for U.S. Appl. No. 13/078,091, filed Apr. 1, 2011 and issued as U.S. Pat. No. 8,237,451 on Aug. 7, 2012 (Inventor—Joy; Applicant—CardioMEMS) (pp. 1-1).

Non-Final Office Action issued Jun. 9, 2006 for U.S. Appl. No. 10/943,772, filed Sep. 16, 2004 and published as U.S. 2005/0187482 on Aug. 25, 2005 (Inventor—O'Brien; Applicant—CardioMEMS) (pp. 1-15).

Amendment and Response to Non-Final Office Action filed Oct. 13, 2006 for U.S. Appl. No. 10/943,772, filed Sep. 16, 2004 and published as U.S. 2005/0187482 on Aug. 25, 2005 (Inventor—O'Brien; Applicant—CardioMEMS) (pp. 134).

Final Office Action issued Mar. 7, 2007 for U.S. Appl. No. 10/943,772, filed Sep. 16, 2004 and published as U.S. 2005/0187482 on Aug. 25, 2005 (Inventor—O'Brien; Applicant—CardioMEMS) (pp. 1-19).

Preliminary Amendment filed Jun. 21, 2006 for U.S. Appl. No. 11/232,534, filed Sep. 22, 2005 and published as U.S. 2006/0287700 on Dec. 21, 2006 (Inventor—White; Applicant—CardioMEMS) (pp. 1-4).

Non-Final Office Action issued Oct. 18, 2008 for U.S. Appl. No. 11/232,534, filed Sep. 22, 2005 and published as U.S. 2006/0287700 on Dec. 21, 2006 (Inventor—White; Applicant—CardioMEMS) (pp. 1-11).

Response to Non-Final Office Action filed Apr. 15, 2009 for U.S. Appl. No. 11/232,534, filed Sep. 22, 2005 and published as U.S. 2006/0287700 on Dec. 21, 2006 (Inventor—White; Applicant—CardioMEMS) (pp. 1-15).

Final Office Action issued Jul. 10, 2009 for U.S. Appl. No. 11/232,534, filed Sep. 22, 2005 and published as U.S. 2006/0287700 on Dec. 21, 2006 (Inventor—White; Applicant—CardioMEMS) (pp. 1-12).

Notice of Abandonment issued Feb. 16, 2010 for U.S. Appl. No. 11/232,534, filed Sep. 22, 2005 and published as U.S. 2006/0287700 on Dec. 21, 2006 (Inventor—White; Applicant—CardioMEMS) (pp. 1-2).

International Search Report issued Jul. 28, 2006 for International Patent Application No. PCT/US2006/007790, which was filed on Mar. 6, 2006 and published as WO 2006/096582 on Sep. 14, 2006 (Inventor—Allen; Applicant—CardioMEMS) (pp. 1-3).

Supplementary European Search Report issued Feb. 1, 2012 for EP Patent Application No. 05805691.2, which was filed on Oct. 4, 2005 and published as EP 1817593 on Aug. 15, 2007 (Inventor—James; Applicant—CardioMEMS) (pp. 1-7).

Final Office Action issued Mar. 26, 2012 for U.S. Appl. No. 12/612,070, filed Nov. 4, 2009 and published as U.S. 2010/0058583 on Mar. 11, 2010 (Inventor—Cros; Applicant—CardioMEMS) (pp. 1-8).

Notice of Allowance issued Mar. 23, 2009 for U.S. Appl. No. 11/204,812, filed Aug. 16, 2005 and issued as U.S. Pat. No. 7,621,036 on Nov. 24, 2009 (Inventor—Cros; Applicant—CardioMEMS) (pp. 1-7).

(56) References Cited

OTHER PUBLICATIONS

Requirement for Restriction issued May 10, 2012 for U.S. Appl. No. 12/509,053, filed Jul. 24, 2009 and published as U.S. 2010/0022896 on Jan. 28, 2010 (Inventor—Yadav; Applicant—CardioMEMS) (pp. 1-7).
Response to Restriction Requirement filed May 17, 2012 for U.S. Appl. No. 12/509,053, filed Jul. 24, 2009 and published as U.S. 2010/0022896 on Jan. 28, 2010 (Inventor—Yadav; Applicant—CardioMEMS) (pp. 1-3).
Non-Final Office Action issued Aug. 2, 2012 for U.S. Appl. No. 12/509,053, filed Jul. 24, 2009 and published as U.S. 2010/0022896 on Jan. 28, 2010 (Inventor—Yadav; Applicant—CardioMEMS) (pp. 1-13).
Response to Non-Final Office Action filed Feb. 4, 2014 for U.S. Appl. No. 12/509,053, filed Jul. 24, 2009 and published as U.S. 2010/0022896 on Jan. 28, 2010 (Inventor—Yadav; Applicant—CardioMEMS) (pp. 118).
Final Office Action issued Jun. 3, 2013 for U.S. Appl. No. 12/509,053, filed Jul. 24, 2009 and published as U.S. 2010/0022896 on Jan. 28, 2010 (Inventor—Yadav; Applicant—CardioMEMS) (pp. 1-6).
Response to Final Office Action filed Dec. 2, 2013 for U.S. Appl. No. 12/509,053, filed Jul. 24, 2009 and published as U.S. 2010/0022896 on Jan. 28, 2010 (Inventor—Yadav; Applicant—CardioMEMS) (pp. 1-12).
Requirement for Restriction issued Dec. 12, 2006 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-7).
Response to Restriction Requirement filed Jan. 10, 2007 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-5).
Notice of Allowance issued Feb. 14, 2007 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-3).
Request for Continued Examination filed May 14, 2007 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-1).
Notice of Allowance issued Jun. 18, 2007 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-2).
Examiner Interview Summary issued Jul. 23, 2007 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-2).
Notice of Allowance issued Jul. 23, 2007 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-3).
Request for Continued Examination filed Oct. 23, 2007 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-1).
Notice of Allowance issued Nov. 21, 2007 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-3).
Request for Continued Examination filed Feb. 21, 2008 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-3).
Notice of Allowance issued Mar. 5, 2008 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-6).
Request for Continued Examination filed Jun. 5, 2008 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-3).
Notice of Allowance issued Jun. 13, 2008 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-6).
Request for Continued Examination filed Sep. 10, 2008 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-3).
Notice of Allowance issued Oct. 7, 2008 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-6).
Issue Notification issued Feb. 11, 2009 for U.S. Appl. No. 11/276,571, filed Mar. 6, 2006 and issued as U.S. Pat. No. 7,498,799 on Mar. 3, 2009 (Inventor—Allen; Applicant—CardioMEMS) (pp. 1-1).

\* cited by examiner

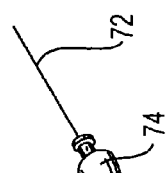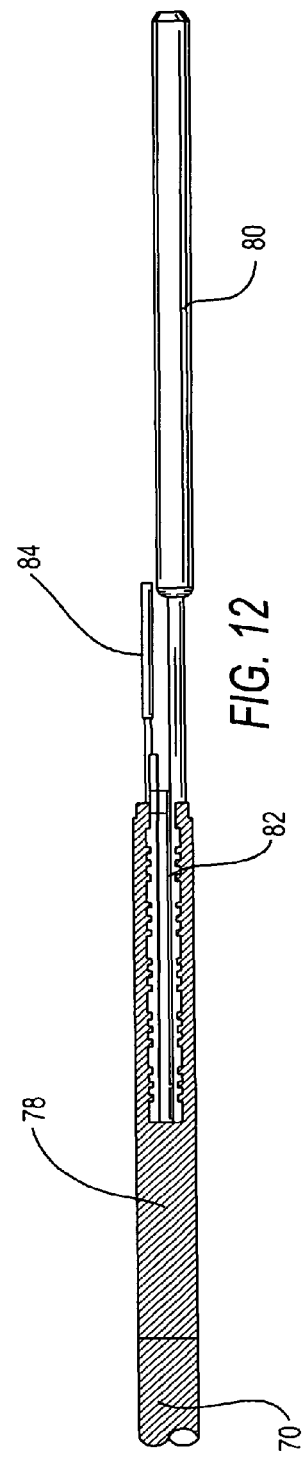

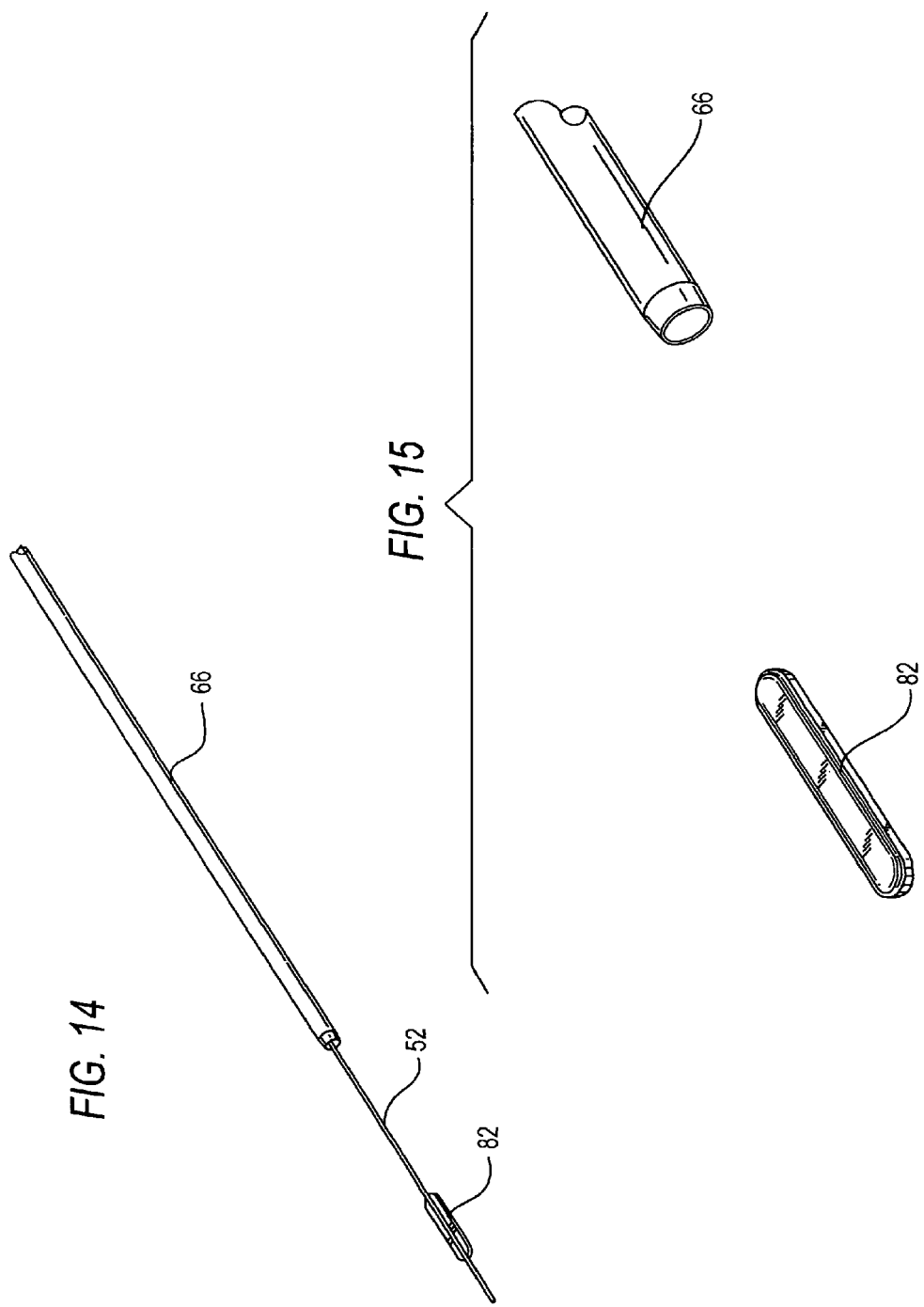

IMPLANTABLE WIRELESS SENSOR

CROSS-REFERENCE TO RELATED APPLICATION

This application is a divisional application of U.S. patent application Ser. No. 11/472,905, filed Jun. 22, 2006, now U.S. Pat. No. 7,574,792 which is a divisional application of U.S. patent application Ser. No. 10/943,772, filed Sep. 16, 2004, now abandoned, which is based upon commonly assigned U.S. provisional patent application Ser. No. 60/503,745, filed Sep. 16, 2003, incorporated herein by reference in its entirety.

FIELD OF THE INVENTION

The application is directed to an implantable wireless sensor. More particularly, this invention is directed to a wireless, unpowered, micromechanical sensor that can be delivered using endovascular techniques, to measure a corporeal parameter such as pressure or temperature.

BACKGROUND OF THE INVENTION

Abdominal aortic aneurysms represent a dilatation and weakening of the abdominal aorta which can lead to aortic rupture and sudden death. Previously, the medical treatment of abdominal aortic aneurysms required complicated surgery with an associated high risk of injury to the patient. More recently, endografts (combining stents and grafts into a single device) have been developed that can be inserted through small incisions in the groin. Once in place, these endografts seal off the weakened section of the aorta. The aneurysms can then heal, eliminating the risk of sudden rupture. This less invasive form of treatment for abdominal aortic aneurysms has rapidly become the standard of care for this disease. An example of an endograft device is disclosed in Kornberg, U.S. Pat. No. 4,617,932.

A significant problem with endografts is that, due to inadequate sealing of the graft with the aorta, leaks can develop that allow blood to continue to fill the aneurysmal sac. Left undiscovered, the sac will continue to expand and potentially rupture. To address this situation, patients who have received endograft treatment for their abdominal aortic aneurysms are subjected to complex procedures that rely on injection of contrast agents to visualize the interior of the aneurysm sac. These procedures are expensive, not sensitive, and painful. In addition, they subject the patient to additional risk of injury. See, for example, Baum R A et al., "Aneurysm sac pressure measurements after endovascular repair of abdominal aortic aneurysms," *The Journal of Vascular Surgery*, January 2001, and Schurink G W et al., "Endoleakage after stent-graft treatment of abdominal aneurysm: implications on pressure and imaging—an in vitro study," *The Journal of Vascular Surgery*, August 1998. These articles provide further confirmation of the problem of endograft leakage and the value of intra-sac pressure measurements for monitoring of this condition.

Thus, there is a need for a method of monitor the pressure within an aneurysm sac that has undergone repair by implantation of an endograft to be able to identify the potential presence of endoleaks. Furthermore, this method should be accurate, reliable, safe, simple to use, inexpensive to manufacture, convenient to implant and comfortable to the patient.

An ideal method of accomplishing all of the above objectives would be to place a device capable of measuring pressure within the aneurysm sac at the time of endograft insertion. By utilizing an external device to display the pressure being measured by the sensor, the physician will obtain an immediate assessment of the success of the endograft at time of the procedure, and outpatient follow-up visits will allow simple monitoring of the success of the endograft implantation.

An example of an implantable pressure sensor designed to monitor pressure increases within an aneurysmal sac is shown in Van Bockel, U.S. Pat. No. 6,159,156. While some of the above objectives are accomplished, this device has multiple problems that would make its use impractical. For example, the sensor system disclosed in the Van Bockel patent relies on a mechanical sensing element that cannot be practically manufactured in dimensions that would allow for endovascular introduction. In addition, this type of pressure sensor would be subject to many problems in use that would limit its accuracy, stability and reliability. One example would be the interconnection of transponder and sensor as taught by Van Bockel, such interconnection being exposed to body fluids which could disrupt its function. This would impact the device's ability to maintain accurate pressure reading over long periods of time. A fundamental problem with sensors is their tendency to drift over time. A sensor described in the Van Bockel patent would be subject to drift as a result of its failure to seal the pressure sensing circuit from the external environment. Also, by failing to take advantage of specific approaches to electronic component fabrication, allowing for extensive miniaturization, the Van Bockel device requires a complex system for acquiring data from the sensor necessary for the physician to make an accurate determination of intra-aneurysmal pressure.

OBJECTS OF THE INVENTION

It is an object of this invention to provide an implantable wireless sensor.

It is also an object of this invention to provide a wireless, unpowered, micromechanical sensor that can be delivered endovascularly.

It is a further object of this invention to provide an implantable, wireless, unpowered sensor that can be delivered endovascularly to measure pressure and/or temperature.

It is a yet further object of this invention to provide a method of preparing a micromechanical implantable sensor.

It is a yet further object of this invention to provide a micromechanical sensor with a hermetically sealed, unbreached pressure reference for enhanced stability.

These and other objects of the invention will become more apparent from the discussion below.

SUMMARY OF THE INVENTION

The present invention comprises a method for manufacturing a device that can be implanted into the human body using non-surgical techniques to measure a corporeal parameter such as pressure, temperature, or both. Specific target locations could include the interior of an abdominal aneurysm or a chamber of the heart. This sensor is fabricated using Micro-ElectroMechanical Systems (MEMS) technology, which allows the creation of a device that is small, accurate, precise, durable, robust, biocompatible, radiopaque and insensitive to changes in body chemistry, biology or external pressure. This device will not require the use of wires to relay pressure information externally nor need an internal power supply to perform its function.

Stated somewhat more specifically, according to the disclosed method, a cavity is etched in one side of a first substrate. A conductive central plate and surrounding conductive coil is formed on the base of the cavity. A second conductive central plate and surrounding conductive coil is formed on a surface of a second substrate, and the two substrates are mutually imposed such that the two conductive plates and coils are disposed in opposed, spaced-apart relation. A laser is then used to cut away perimeter portions of the imposed substrates and simultaneously to heat bond the two substrates together such that the cavity in the first substrate is hermetically sealed.

According to one embodiment of the invention, the second conductive plate and coil are formed on the upper surface of the second substrate. According to another embodiment, the second substrate has a cavity etched into its upper side, and the conductive plate and coil are formed on the base of the cavity. According to this second embodiment, when the two substrates are mutually imposed, the cavities in the respective substrates communicate to form a hollow. The subsequent laser operation hermetically seals the hollow within the sensor body.

BRIEF DESCRIPTION OF THE DRAWINGS

FIGS. 9 to 12 show additional details of the tethering system;

FIGS. 13 to 15 show details of the delivery system;

DETAILED DESCRIPTION OF THE INVENTION

Figure 1:
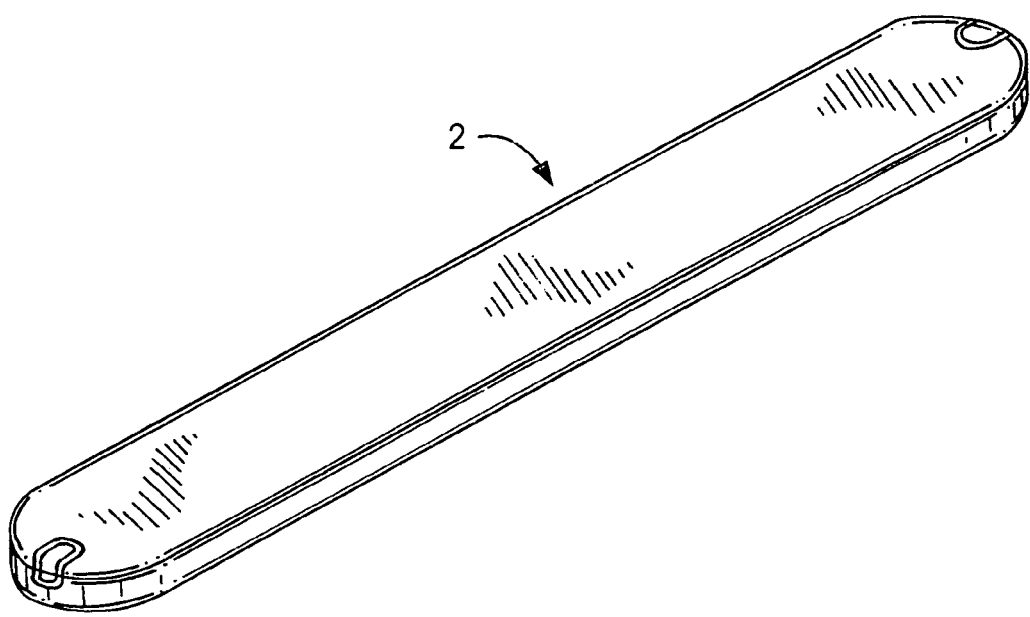
FIG. 1 is an oblique perspective view of an embodiment of the invention.

The invention can perhaps be better understood by referring to the drawings. FIG. 1 is an oblique, perspective view of a sensor 2, an embodiment of the invention. Sensor 2 preferably has an outer coating of biocompatible silicone.

Figure 2:
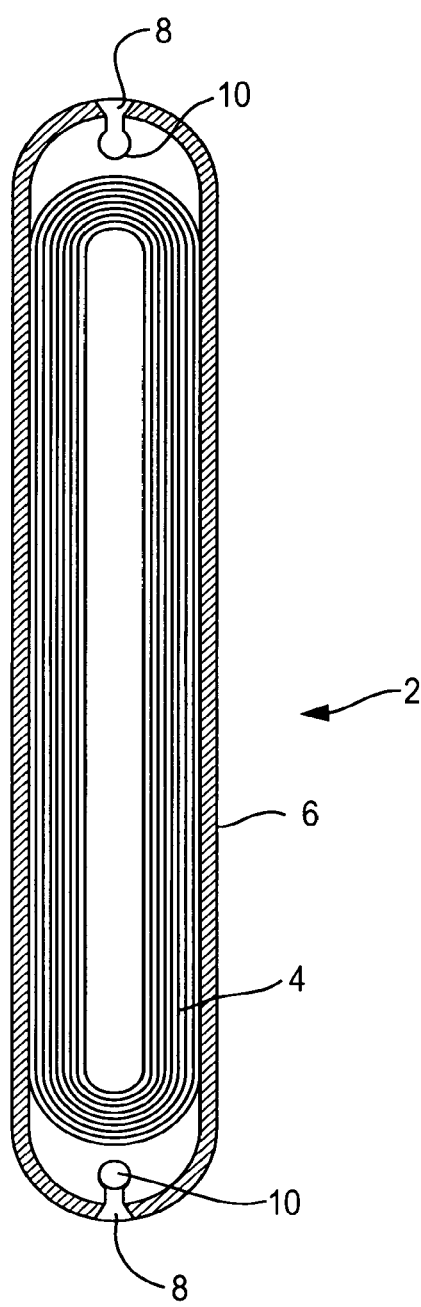
FIG. 2 is a top, partly cross-sectional view of the embodiment of the invention shown in FIG. 1.

FIG. 2 is a top, partial cross-section of a schematic representation of sensor 2 where a wire spiral inductor coil 4 is positioned in planar fashion in a substrate 6. Optionally sensor 2 may have recesses 8, each with a hole 10, to receive a tether wire (not shown here) for delivery of the device into a human patient, as described below.

Figure 3:
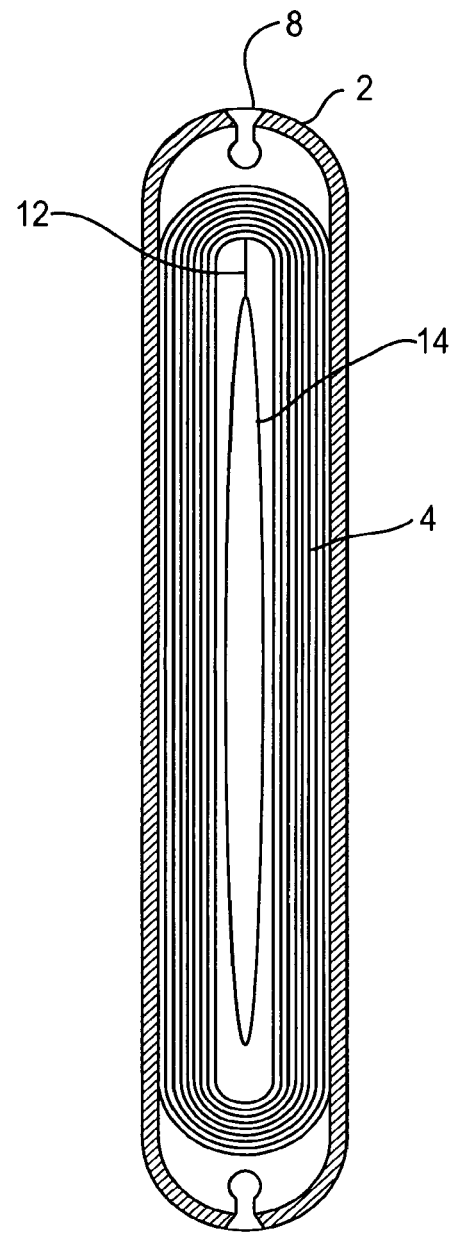
FIG. 3 is a top, partly cross-sectional view of another embodiment of the invention.

In the embodiment of the invention shown in FIG. 3, a wire 12 connects coil 4 to a capacitor plate 14 positioned within coil 4.

Figure 4:
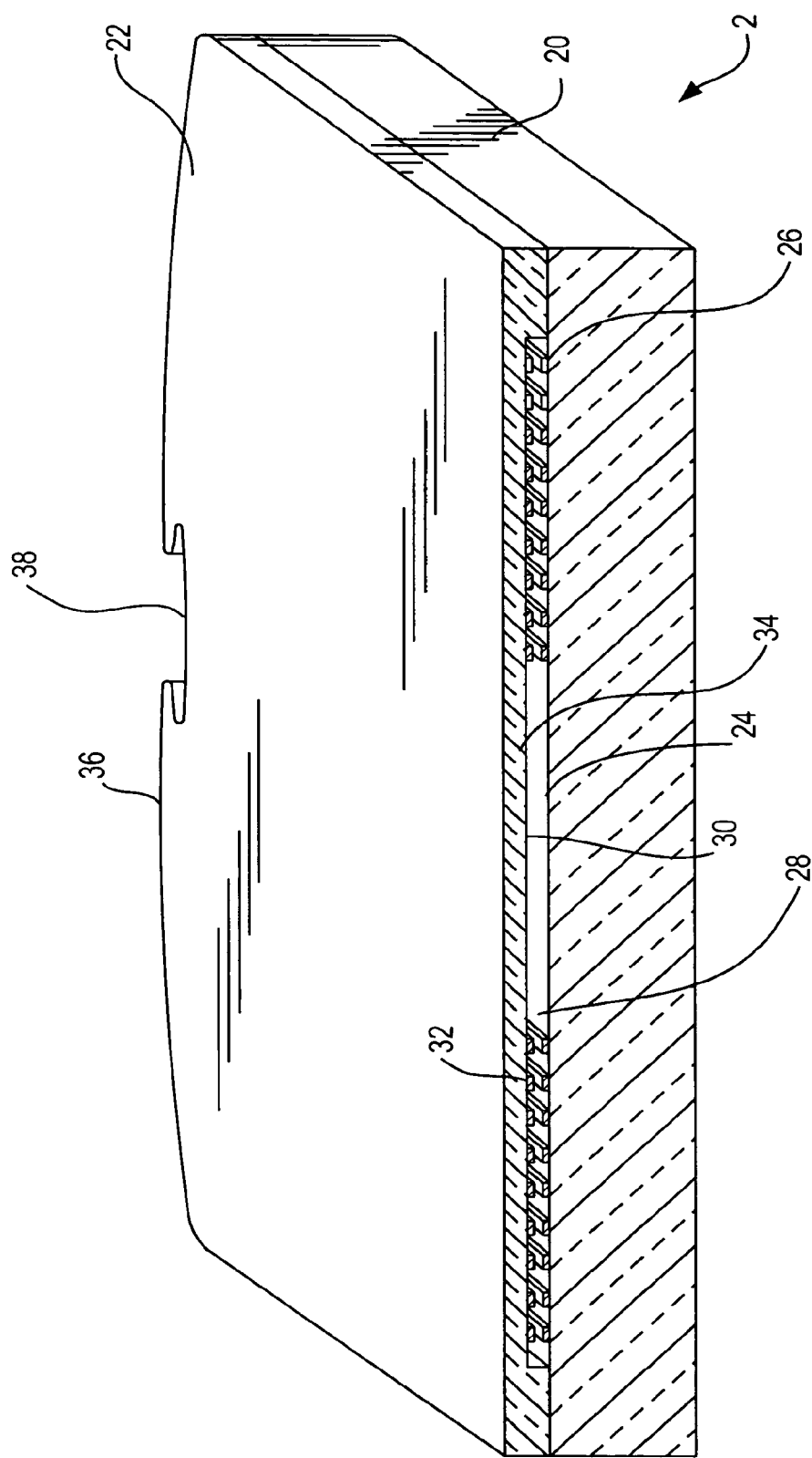
FIG. 4 is an oblique, cross-sectional view of the embodiment of the invention shown in FIG. 2.

FIG. 4 is a slightly oblique cross-section across its width of the embodiment of the invention shown in FIG. 2, where it can be seen that sensor 2 is comprised of a lower substrate 20 and an upper substrate 22. Lower substrate 20 and upper substrate 22 are constructed from a suitable material, such as glass, fused silica, sapphire, quartz, or silicon. Fused silica is the preferred material of construction. Lower substrate 20 has on its upper surface 24 an induction coil 26, and upper substrate 22 has a recess 28 with a surface 30 having an induction coil 32 thereon. The top surface of upper substrate 22 forms a membrane 34 capable of mechanically responding to changes in a patient's physical property, such as pressure. The end 36 of sensor 2 has a notch or recess 38.

Figure 5:
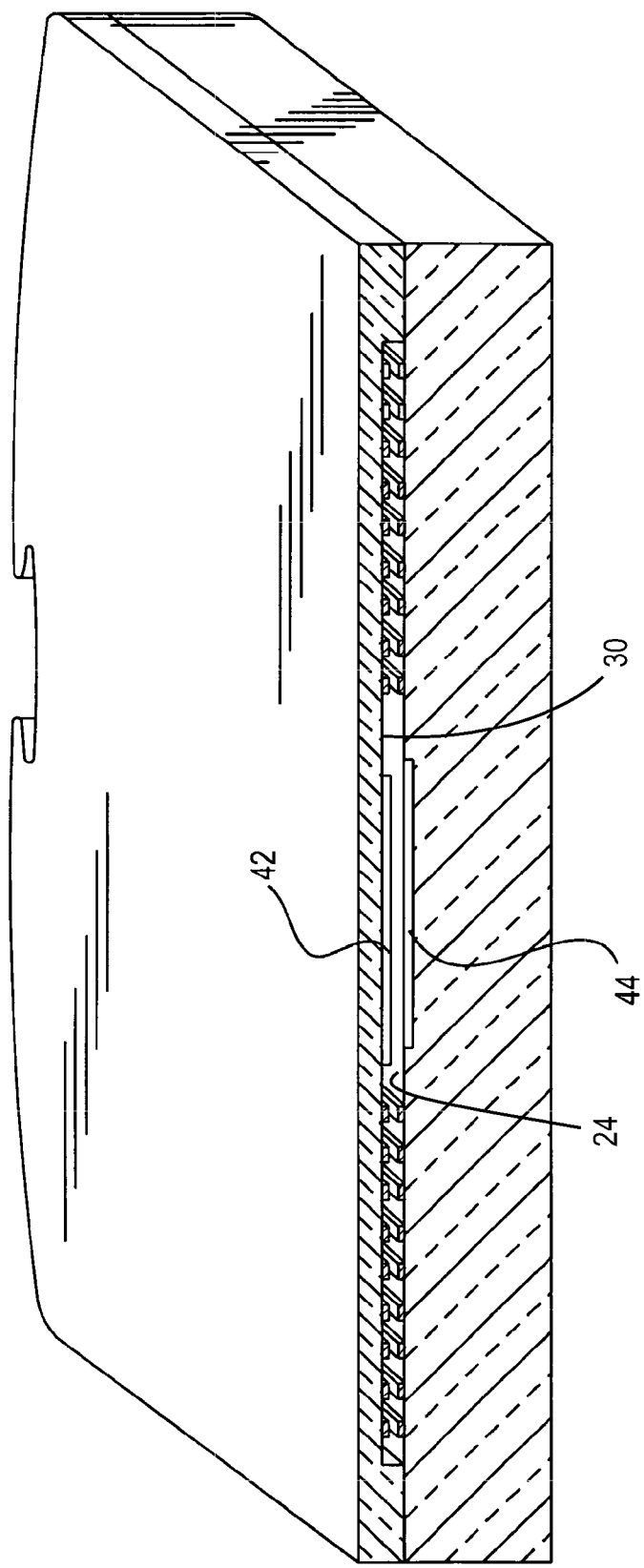
FIG. 5 is an oblique, cross-sectional view of the embodiment of the invention shown in FIG. 3.

In similar fashion, FIG. 5 is a slightly oblique cross-section across its width of the embodiment of the invention shown in FIG. 3. The primary difference between FIGS. 4 and 5 is the presence of upper capacitor plate 42 and lower capacitor plate 44 on surfaces 24 and 30, respectively. In the embodiment of FIG. 4, the spiral coil 4 itself acts as the capacitive element of the LC circuit that describes the operation of the sensor.

Figure 6:
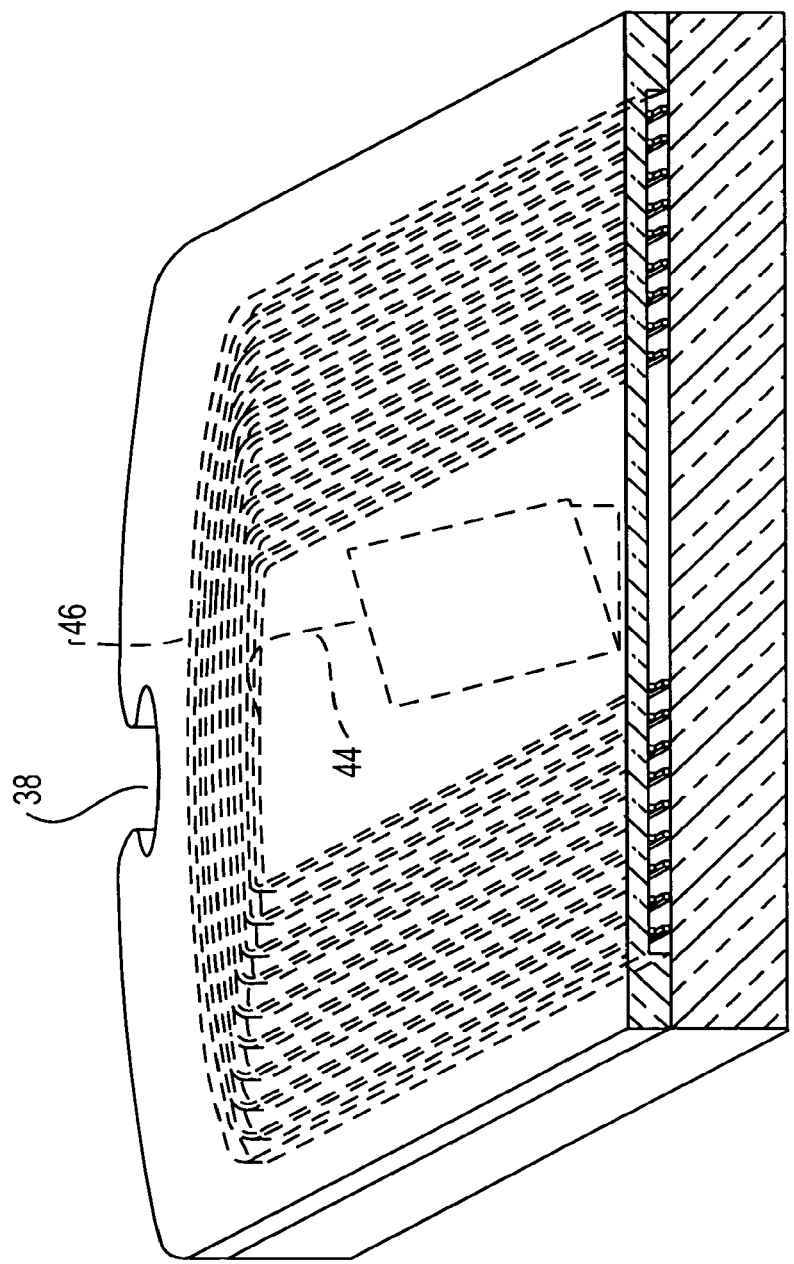
FIG. 6 is a exposed cross-sectional view of the embodiment of the invention shown in FIG. 5.

FIG. 6 is a variation of FIG. 5 where the outline of upper substrate 22 is shown but the details of lower substrate 20 can be seen more clearly, including individual coils of inductor coil 26. A wire 46 connects lower capacitor plate 44 to induction coil 26.

The size of the sensors of the invention will vary according to factors such as the intended application, the delivery system, etc. The oval sensors are intended to be from about 0.5 in. to about 1 in. in length and from about 0.1 in. to about 0.5 in. in width, with a thickness of from about 0.05 in. to about 0.30 in.

As shown in FIGS. 4 and 5, upper substrate 22 can be significantly thinner than lower substrate 20. By way of example, upper substrate 22 may be from about 100 to about 300 microns thick, whereas lower substrate 20 may be from about 500 to about 1500 microns thick. In an alternate embodiment of the invention, both substrates may be of the same thickness ranging from about 100 to about 1000 microns.

Figure 7:
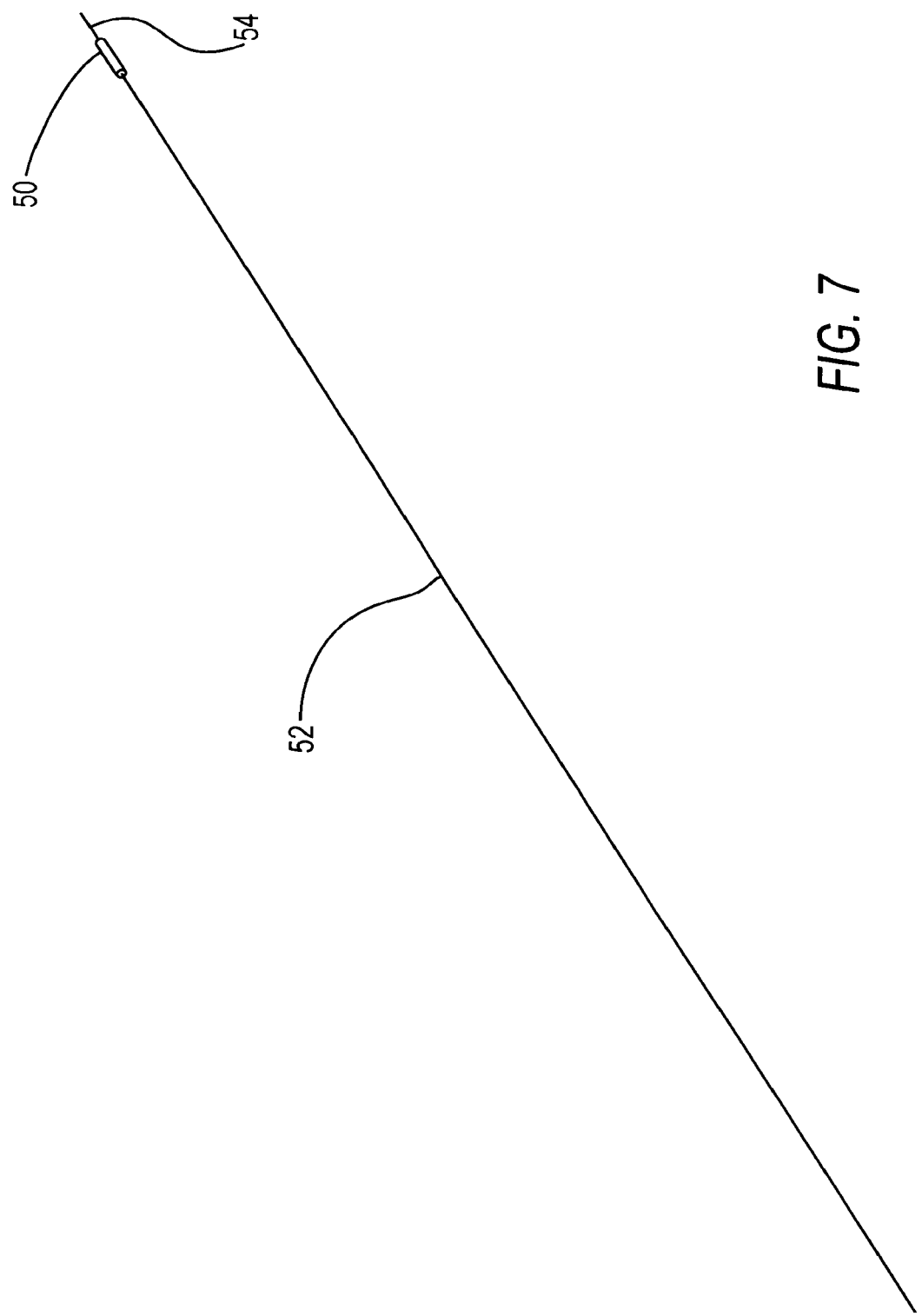
FIG. 7 shows part of the sensor tethering system.

In the embodiment of the invention shown in FIG. 7, a sensor 50 is attached to a hollow tube 52 that has a flexible tip 54.

Figure 8:
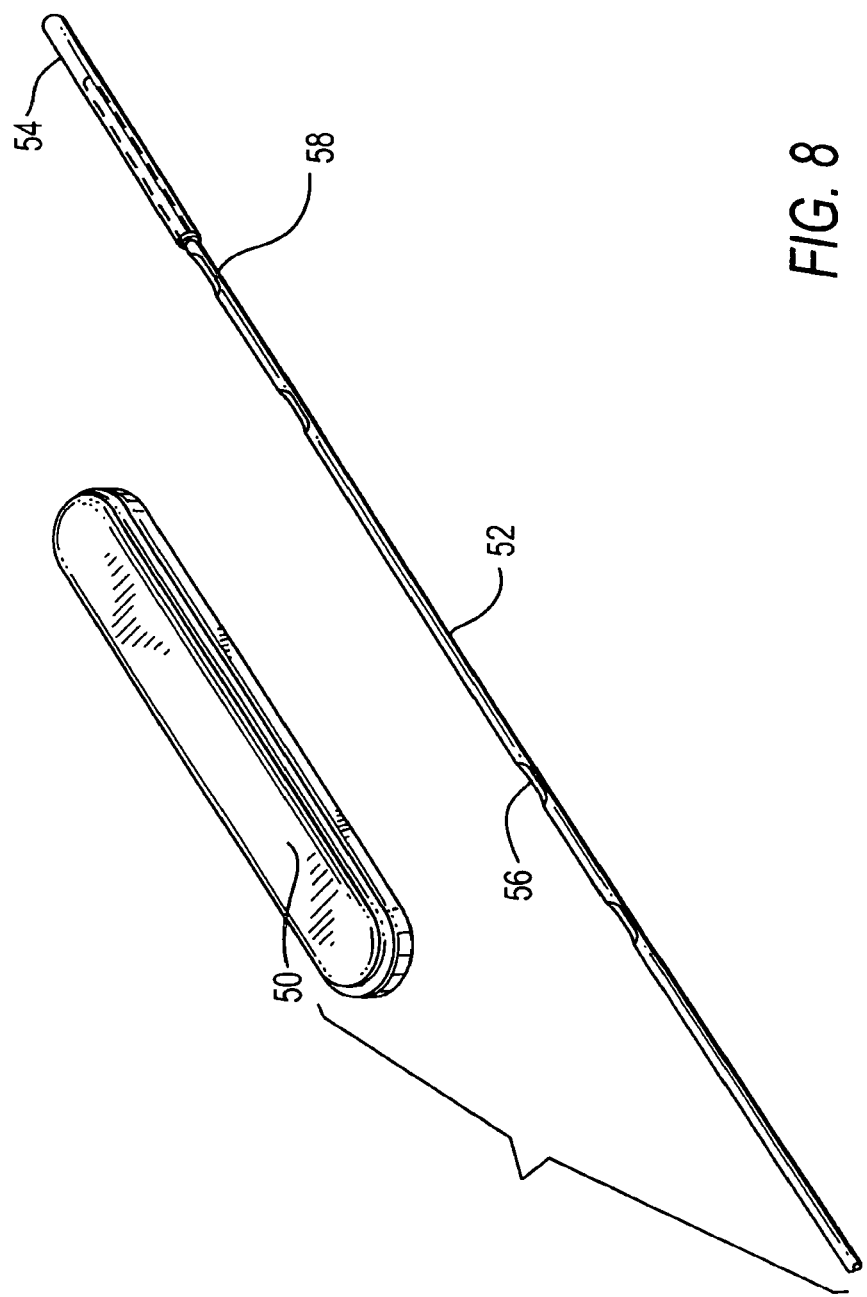
FIG. 8 shows the further details of the tethering system.

FIG. 8 shows the sensor 50 and specific features of the tethering system, namely proximal holes 56 and distal holes 58 disposed in a hollow tube 52.

Figure 9:
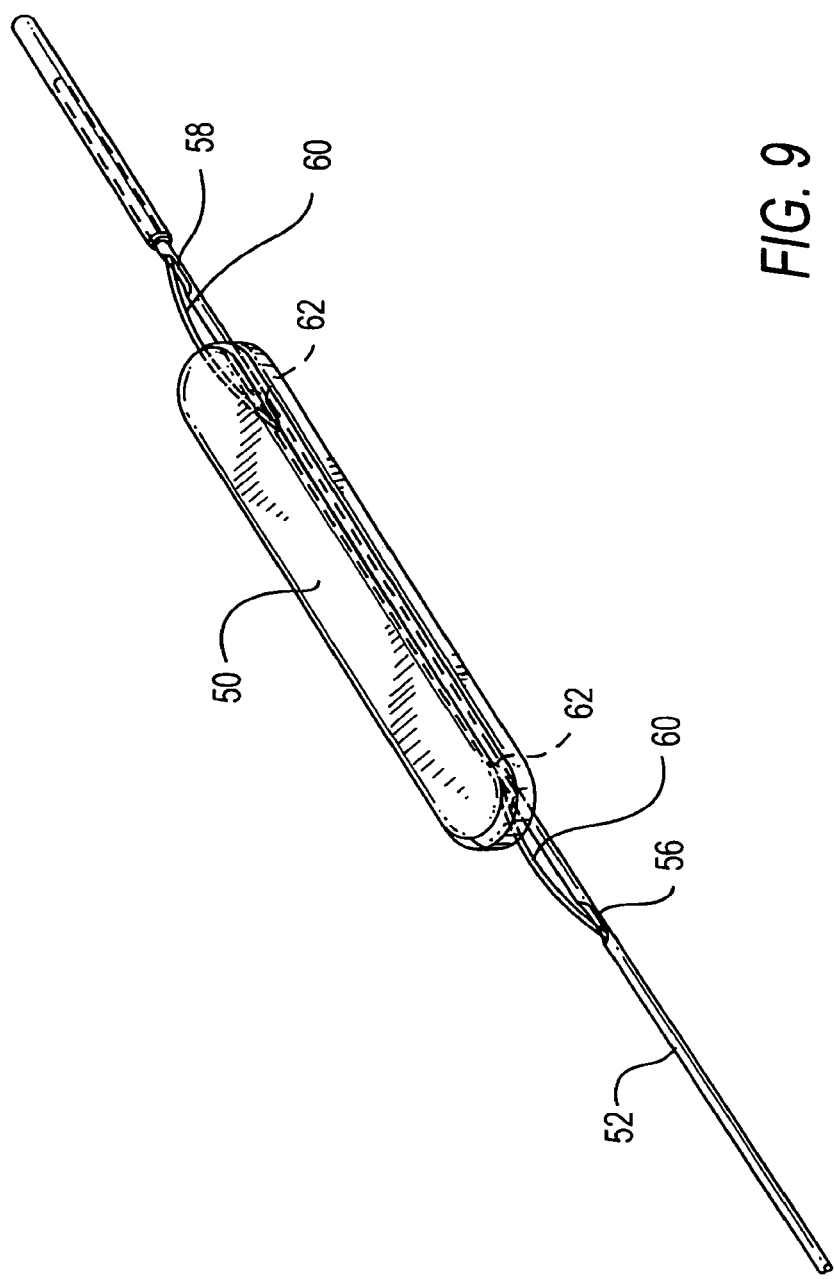

FIG. 9 shows a tether wire 60 that is attached to sensor 50 at sensor holes 62 and hollow tube holes 56 and 58, and a tether wire 60 is positioned slidably within a hollow tube 52.

Figure 10:
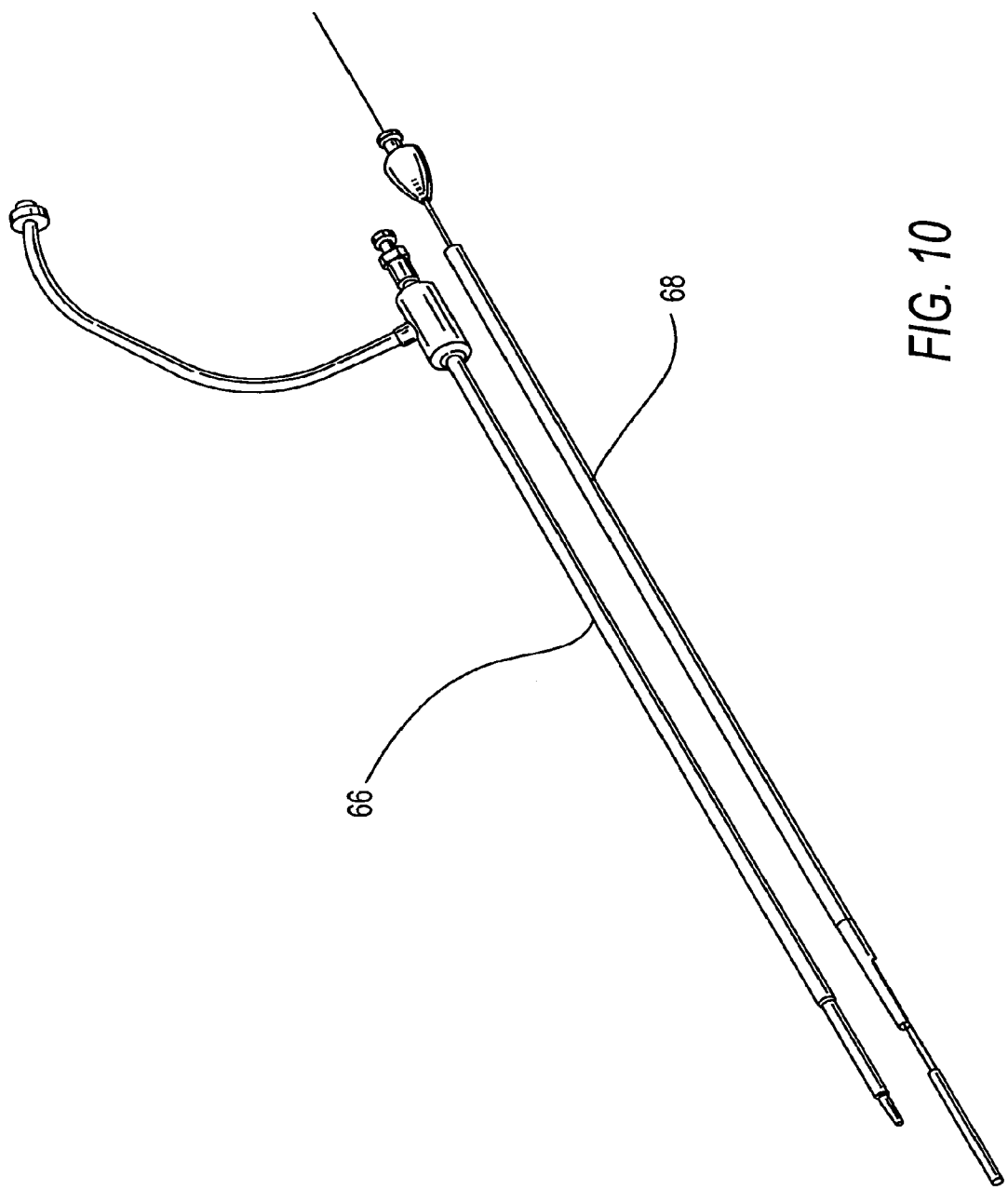

A better appreciation of certain aspects of the invention, especially of a delivery system, can be obtained from FIG. 10 which shows a vessel introducer 66 and the delivery system 68.

Further details of the delivery system are shown in FIG. 11. A double lumen tube 70 has one channel that accepts a guidewire 72 and a second channel that accepts the sensor tether wire. The guidewire 72 can be advanced through hub 74. A rigid delivery capsule 78 is disposed at the far end of the delivery catheter and flexible tip 80 is connected to the catheter via a hollow tube 81 extending through the delivery capsule 78. A sensor 82 is positioned inside a slot in the delivery capsule 78 proximal to flexible tip 80.

FIG. 12 shows a lateral, cross-sectional view of this arrangement where the sensor 82 is inside the slot of delivery capsule 78 and the flexible tip 84 of the tether wire is disposed between the end of delivery capsule 78 and flexible tip 80.

Figure 13:
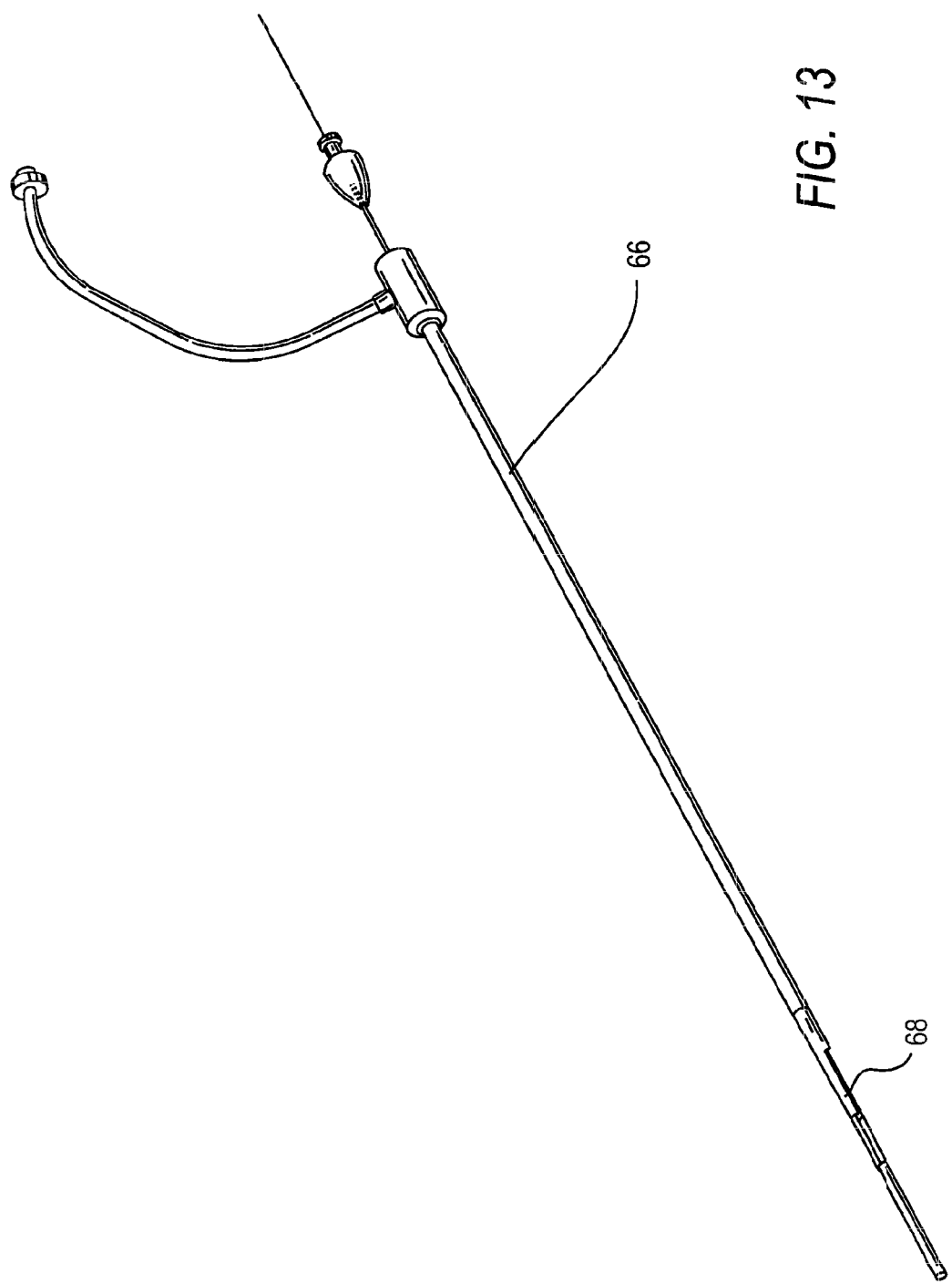

FIG. 13 shows delivery catheter 68 loaded into the previously placed vessel introducer 66 prior to introduction of the sensor into the body.

FIG. 14 shows that the sensor 82 on tether tube 52 has been advanced out of delivery capsule 78 and the delivery catheter has been removed.

In FIG. 15, the tether wire has been retracted into the hollow tether tube, releasing the sensor. The tether wire, tether tube and vessel introducer 66 are then all removed.

The pressure sensor of the invention can be manufactured using Micro-machining techniques that were developed for the integrated circuit industry. An example of this type of sensor features an inductive-capacitive (LC) resonant circuit with a variable capacitor, as is described in Allen et al., U.S. Pat. Nos. 6,111,520 and 6,278,379, all of which are incorporated herein by reference. The sensor contains two types of passive electrical components, namely, an inductor and a capacitor. The sensor is constructed so that the fluid pressure at the sensor's surface changes the distance between the capacitor's substantially parallel plates and causes a variation of the sensor's capacitance.

In a preferred embodiment the sensor of the invention is constructed through a series of steps that use standard MEMS manufacturing techniques.

Figure 16:
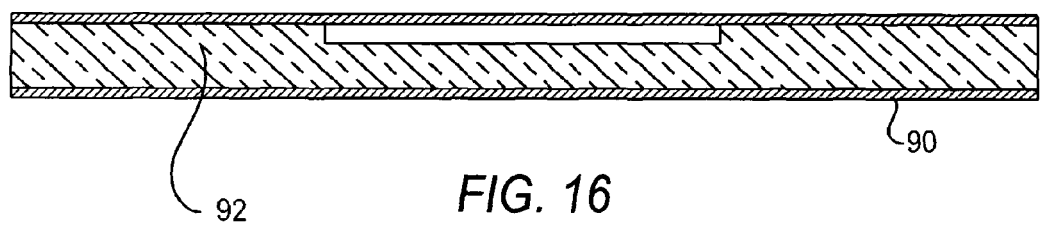
FIGS. 16 to 26 show details of the manufacturing process used to fabricate the invention.

FIG. 16 shows the first step of this process in which a thin layer of metal (Protective mask) 90 is deposited onto the top and bottom surface of a fused silica substrate 92 (alternative materials would be glass, quartz, silicon or ceramic). Substrate diameters can range from about 3 to about 6 in. Substrate thickness can range from about 100 to about 1500 microns. A pattern mask is then created on one side of the substrate to define the location of cavities that need to be etched into the surface.

Figure 17:
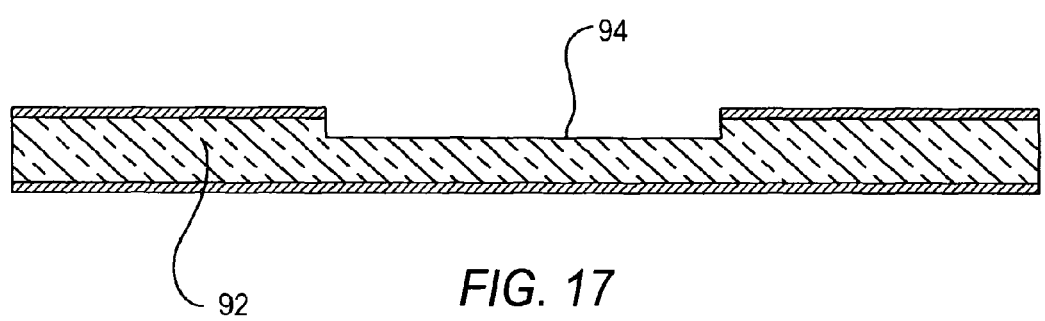

FIG. 17 shows trenches or cavities 94 are etched into one surface of the substrate 92 to depths ranging from about 20 to about 200 microns. This etching is accomplished using any combination of standard wet and dry etching techniques (acid etch, plasma etch, reactive ion etching) that are well known in the MEMS industry. The protective metal mask is removed using standard metal etching techniques.

Figure 18:
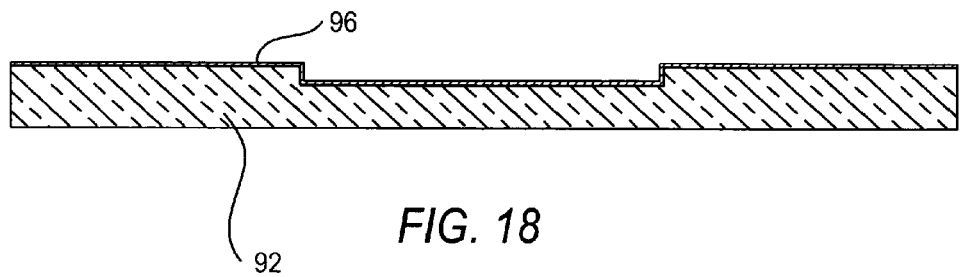

In FIG. 18, a thin metal seed layer 96 (typically chromium) is deposited on the etched side of the substrate using standard metal deposition techniques such as sputtering, plating or metal evaporation.

Figure 19:
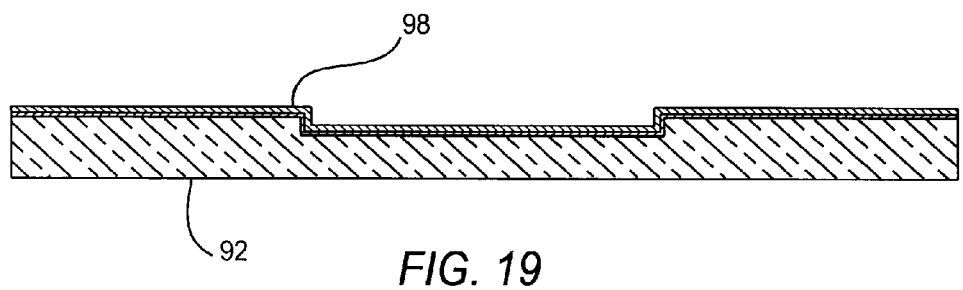

In FIG. 19 a layer of photo-resistive material 98 is applied to the etched surface of the substrate using standard spin coating procedures.

Figure 20:
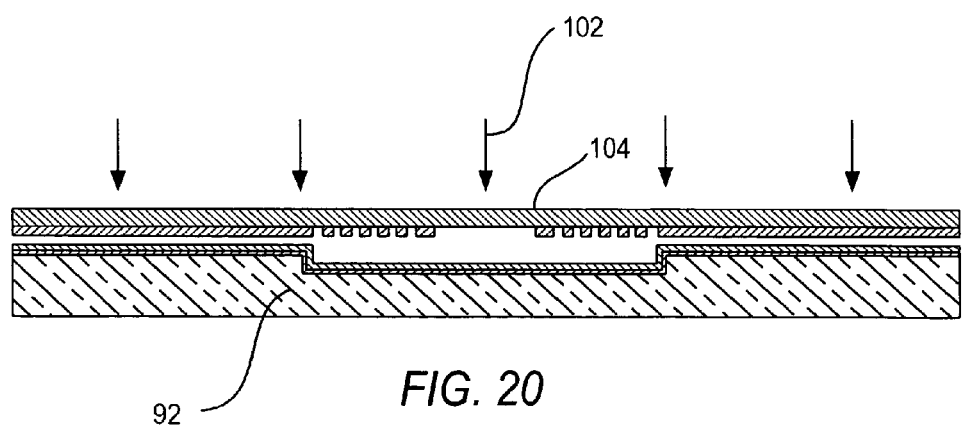

FIG. 20 shows that a mask aligner and UV light 102 is used in a photolithographic processes to transfer a pattern from a mask 104 to the photoresist coating on the substrate.

Figure 21:
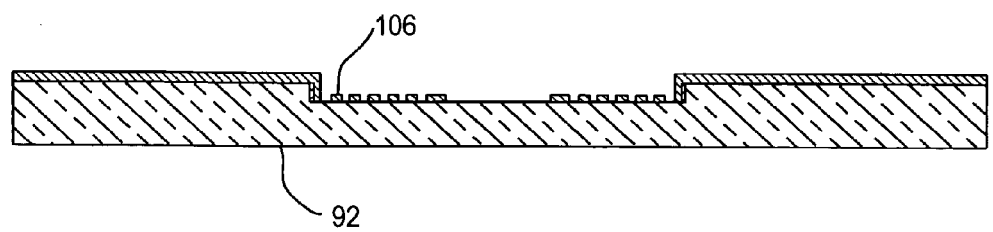

In FIG. 21, the non-masked portions of the Photoresist are removed chemically creating a mold 106 of the desired coil pattern.

Figure 22:
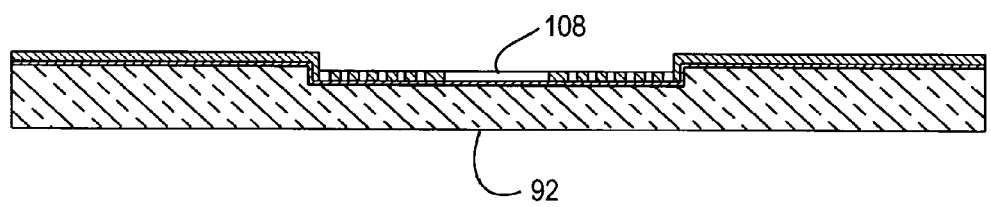

FIG. 22 shows copper 108 electroplated into the mold to the desired height, typically from about 5 to about 35 microns.

Figure 23:
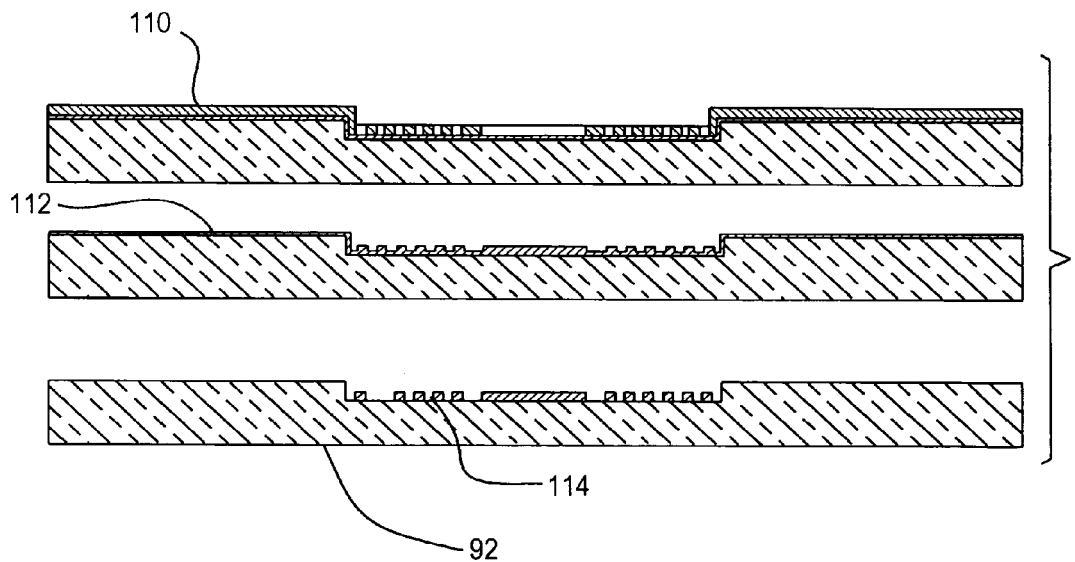

In FIG. 23, the Photoresist 110 and seed layer 112 are etched away leaving the plated copper coils 114.

This process is then repeated with a second substrate.

Figure 24:
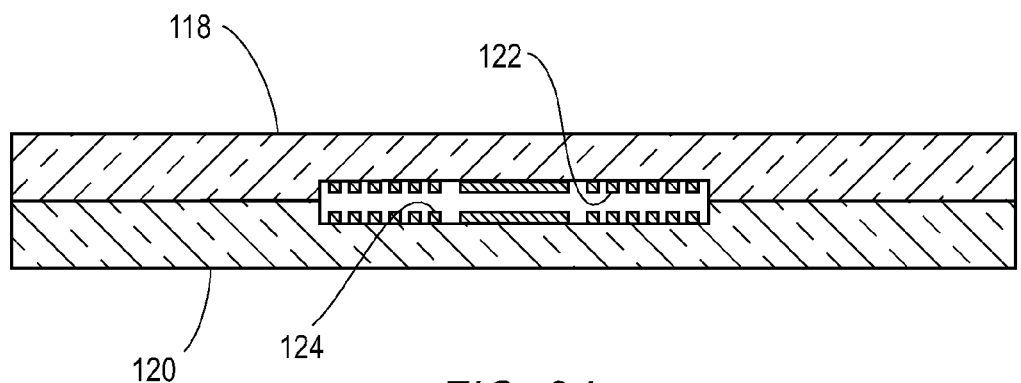

In FIG. 24, the two processed substrates 118 and 120 are aligned such that the cavities 122 and 124 with plated coils are precisely orientated in over one another and temporarily bonded to each other.

Figure 25:
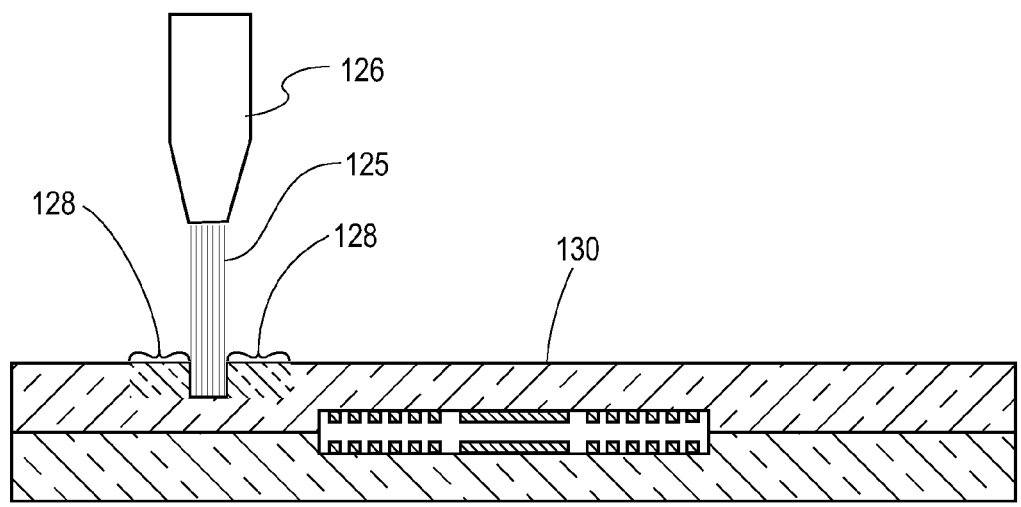
Figure 26:
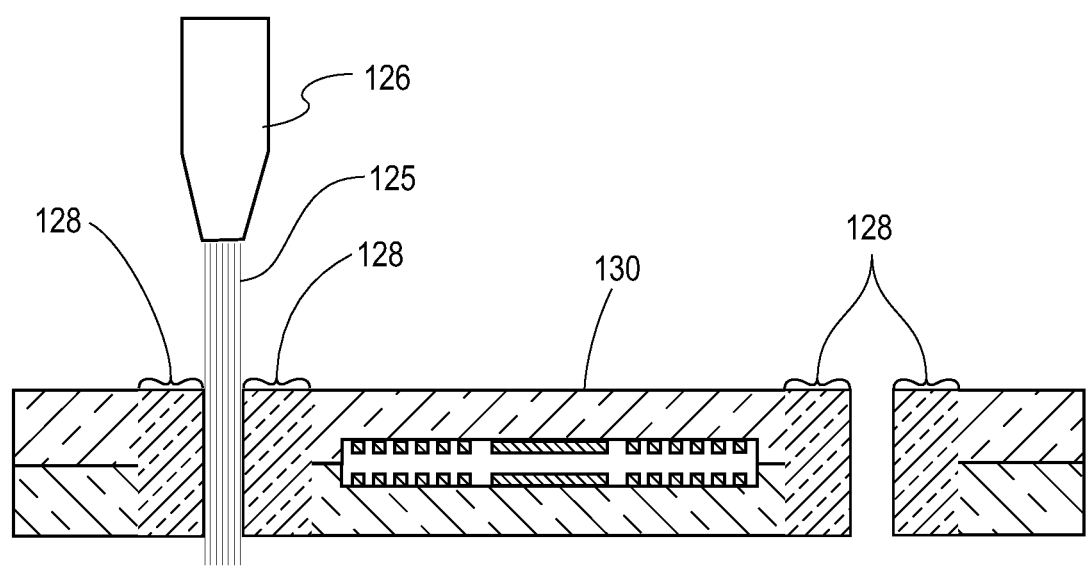

FIGS. 25 and 26 show that by using a beam 125 from a CO2 laser 126 (or other appropriate laser type), the individual sensors 130 are cut from the glass substrate. FIG. 25 shows an early stage in the cutting process where the laser beam 125 has only just begun heating up the surrounding material. FIG. 26 shows a later stage in the process where one side has already been completely cut and sealed, and the laser beam is in the process of cutting and sealing the other side. The laser cutting process results in a permanent, hermetic seal between the two glass substrates. The laser energy is confined to a precise heat effect zone 128 in which the hermetic seal is created.

Figure 27:
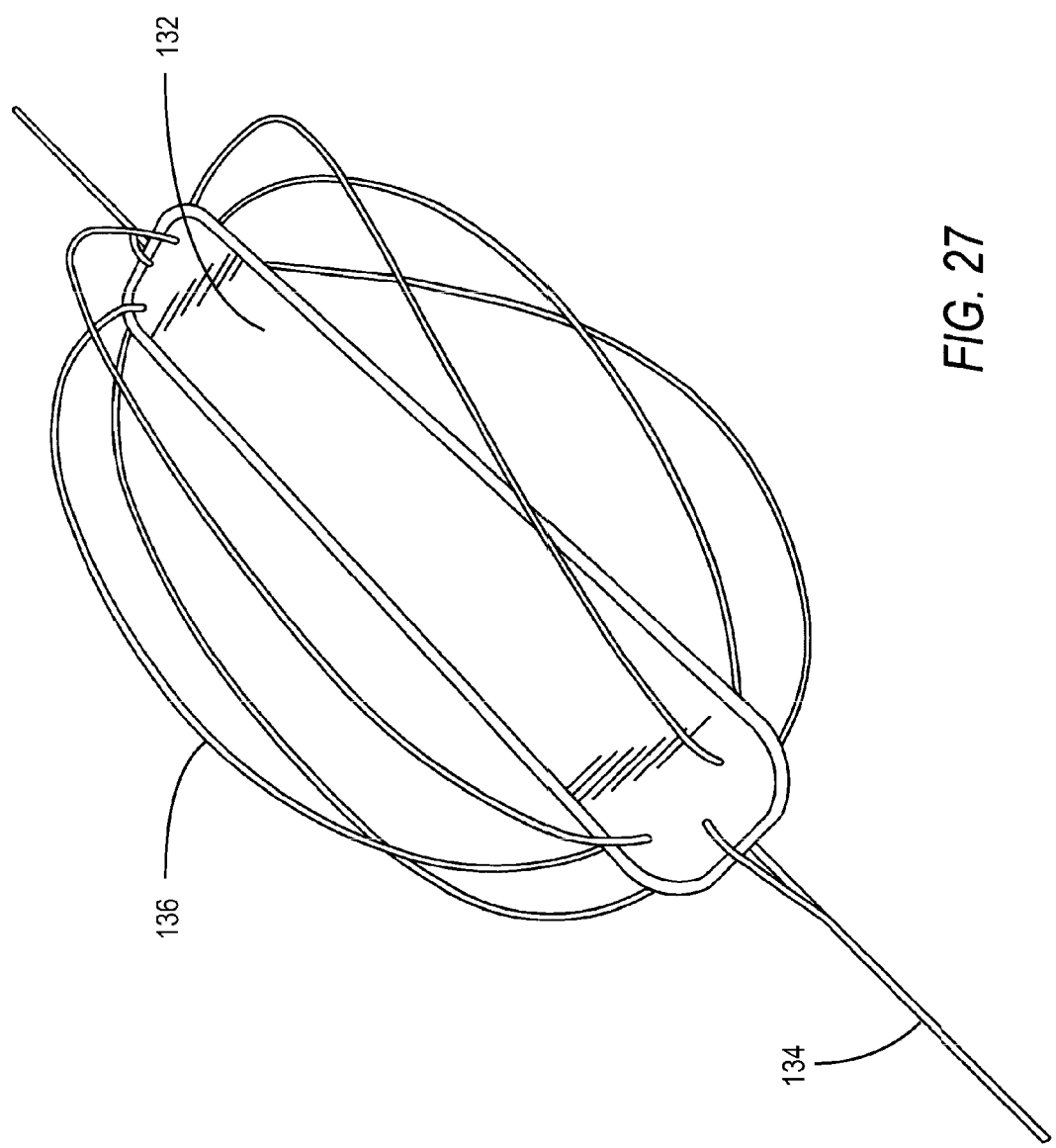
FIG. 27 represents an additional embodiment of the invention.

FIG. 27 represents an embodiment of the invention wherein a sensor 132 attached to a delivery catheter 134 has a stabilizer or basket 136. The stabilizer can be any appropriate device or structure that can be fixedly attached to a sensor of the invention to assist the sensor in maintaining position, location, and/or orientation after the sensor is delivered to an intended site. The stabilizer can comprise any appropriate physiologically acceptable rigid or slightly flexible material, such as stainless steel, nitinol, or a radiopaque metal or alloy.

This sensor design provides many important benefits to sensor performance. The hermetic seal created during the laser cutting process, coupled with the design feature that the conductor lines of the sensor are sealed within the hermetic cavity, allows the sensor to remain stable and drift free during long time exposures to body fluids. In the past, this has been a significant issue to the development of sensors designed for use in the human body. The manufacturing methodology described above allows many variations of sensor geometry and electrical properties. By varying the width of the coils, the number of turns and the gap between the upper and lower coils the resonant frequency that the device operates at and the pressure sensitivity (i.e., the change in frequency as a result of membrane deflection) can be optimized for different applications. In general, the design allows for a very small gap between the coils (typically between about 3 and about 35 microns) that in turn provides a high degree of sensitivity while requiring only a minute movement of the coils to sense pressure changes. This is important for long term durability, where large membrane deflection could result in mechanical fatigue of the pressure sensing element.

The thickness of the sensor used can also be varied to alter mechanical properties. Thicker substrates are more durable for manufacturing. Thinner substrates allow for creating of thin pressure sensitive membranes for added sensitivity. In order to optimize both properties the sensors may be manufactured using substrates of different thicknesses. For example, one side of the sensor may be constructed from a substrate of approximate thickness of 200 microns. This substrate is manufactured using the steps outlined above. Following etching, the thickness of the pressure sensitive membrane (i.e., the bottom of the etched trench) is in the range of from about 85 to about 120 microns.

The matching substrate is from about 500 to about 1000 microns thick. In this substrate, the trench etching step is eliminated and the coils are plated directly onto the flat surface of the substrate extending above the substrate surface a height of from about 20 to about 40 microns. When aligned and bonded, the appropriate gap between the top and bottom coils is created to allow operation preferably in a frequency range of from 30 to 45 MHz and have sensitivity preferably in the range of from 5 to 15 kHz per millimeter of mercury. Due to the presence of the from about 500 to about 1000 micron thick substrate, this sensor will have added durability for endovascular delivery and for use within the human body.

The sensor exhibits the electrical characteristics associated with a standard LC circuit. An LC circuit can be described as a closed loop with two major elements, a capacitor and an inductor. If a current is induced in the LC loop, the energy in the circuit is shared back and forth between the inductor and capacitor. The result is an energy oscillation that will vary at a specific frequency. This is termed the resonant frequency of the circuit and it can be easily calculated as its value is dependent on the circuit's inductance and capacitance. Therefore, a change in capacitance will cause the frequency to shift higher or lower depending upon the change in the value of capacitance.

As noted above, the capacitor in the assembled pressure sensor consists of the two circular conductive segments separated by an air gap. If a pressure force is exerted on these segments it will act to move the two conductive segments closer together. This will have the effect of reducing the air gap between them which will consequently change the capacitance of the circuit. The result will be a shift in the circuit's resonant frequency that will be in direct proportion to the force applied to the sensor's surface.

Because of the presence of the inductor, it is possible to electromagnetically couple to the sensor and induce a current in the circuit. This allows for wireless communication with the sensor and the ability to operate it without the need for an internal source of energy such as a battery. Thus, if the sensor is located within the sac of an aortic aneurysm, it will be possible to determine the pressure within the sac in a simple, non-invasive procedure by remotely interrogating the sensor, recording the resonant frequency and converting this value to a pressure measurement. The readout device generates electromagnetic energy that penetrates through the body's tissues to the sensor's implanted location. The sensor's electrical components absorb a fraction of the electromagnetic energy that is generated by the readout device via inductive coupling. This coupling induces a current in the sensor's circuit that oscillates at the same frequency as the applied electromagnetic energy. Due to the nature of the sensor's electro-mechanical system there exists a frequency of alternating current at which the absorption of energy from the readout device is at a maximum. This frequency is a function of the capacitance of the device. Therefore, if the sensor's capacitance changes, so will the optimal frequency at which it absorbs energy from the readout device. Since the sensor's capacitance is mechanically linked to the fluid pressure at the sensor's surface, a measurement of this frequency by the readout device gives a relative measurement of the fluid pressure. If calibration of the device is performed, then an absolute measurement of pressure can be made. See, for example, the extensive discussion in the Allen et al. patent, again incorporated herein by reference, as well as Gershenfeld et al., U.S. Pat. No. 6,025,725, incorporated herein by reference. Alternative readout schemes, such as phase-correlation approaches to detect the resonant frequency of the sensor, may also be employed.

The pressure sensor is made of completely passive components having no active circuitry or power sources such as batteries. The pressure sensor is completely self-contained having no leads to connect to an external circuit or power source. Furthermore, these same manufacturing techniques can be used to add additional sensing capabilities, such as the ability to measure temperature by the addition of a resistor to the basic LC circuit or by utilizing changes in the back pressure of gas intentionally sealed within the hermetic pressure reference to change the diaphragm position and therefore the capacitance of the LC circuit.

It is within the scope of the invention that the frequency response to the sensor will be in the range of from about 1 to about 200 MHz, preferably from about 1 to about 100 MHz, and more preferably from about 2 to about 90 MHz, and even more preferably from about 30 to about 45 MHz, with a Q factor of from about 5 to about 150, optimally from about 5 to about 80, preferably from about 40 to about 100, more preferably from about 50 to about 90.

In a further embodiment of the invention there is no direct conductor-based electrical connection between the two sides of the LC circuit. Referring again to the sensor described in the Allen et al. patents, the device is constructed using multiple layers upon lie the necessary circuit elements. Disposed on the top and bottom layer are metal patterns constructed using micro-machining techniques which define a top and bottom conductor and a spiral inductor coil. To provide for an electrical contact between the top and bottom layers small vias or holes are cut through the middle layers. When the layers are assembled, a metal paste is forced into the small vias to create direct electrical connections or conduits. However, experimentation has shown that due to additional capacitance that is created between the top and bottom inductor coils, a vialess operational LC circuit can be created. This absence of via holes represents a significant improvement to the sensor in that it simplifies the manufacturing process and, more importantly, significantly increases the durability of the sensor making it more appropriate for use inside the human body.

Further, the invention is not limited to the implantation of a single sensor. Multiple pressure sensors may be introduced into the aneurysm space, each being positioned at different locations. In this situation, each sensor may be designed with a unique signature (obtained by changing the resonant frequency of the sensor), so that the pressure measurement derived from one sensor can be localized to its specific position within the aneurysm.

A significant design factor that relates to the performance of the sensor and the operation of the system is the Quality factor (Q) associated with the sensor. The value of Q is one of the key determinates as to how far from the sensor the external read-out electronics can be located while still maintaining effective communication. Q is defined as a measure of the energy stored by the circuit divided by the energy dissipated by the circuit. Thus, the lower the loss of energy, the higher the Q.

Additional increases in Q can be achieved by removing the central capacitive plate and using capacitive coupling between the copper coils to act as the capacitor element.

In operation, energy transmitted from the external read-out electronics will be stored in the LC circuit of the sensor. This stored energy will induce a current in the LC loop which will cause the energy to be shared back and forth between the inductor and capacitor. The result is an oscillation that will vary at the resonant frequency of the LC circuit. A portion of this oscillating energy is then coupled back to the receiving antenna of the read-out electronics. In high Q sensors, most of the stored energy is available for transmission back to the electronics, which allows the distance between the sensor and the receiving antenna to be increased. Since the transmitted energy will decay exponentially as it travels away from the sensor, the lower the energy available to be transmitted, the faster it will decay below a signal strength that can be detected by the receiving antenna and the closer the sensor needs to be situated relative to the receiving electronics. In general then, the lower the Q, the greater the energy loss and the shorter the distance between sensor and receiving antenna required for sensor detection.

The Q of the sensor will be dependent on multiple factors such as the shape, size, diameter, number of turns, spacing between turns and cross-sectional area of the inductor component. In addition, Q will be greatly affected by the materials used to construct the sensors. Specifically, materials with low loss tangents will provide the sensor with higher Q factors.

The implantable sensor ascending to the invention is preferably constructed of various glasses or ceramics including but not limited to fused silica, quartz, pyrex and sintered zirconia, that provide the required biocompatibility, hermeticity and processing capabilities. Preferably the materials result in a high Q factor. These materials are considered dielectrics, that is, they are poor conductors of electricity, but are efficient supporters of electrostatic or electroquasiatatic fields. An important property of dielectric materials is their ability to support such fields while dissipating minimal energy. The lower the dielectric loss (the proportion of energy lost), the more effective the dielectric material in maintaining high Q. For a lossy dielectric material, the loss is described by the property termed "loss tangent." A large loss tangent reflects a high degree of dielectric loss.

With regard to operation within the human body, there is a second important issue related to Q, namely, that blood and body fluids are conductive mediums and are thus particularly lossy. The consequence of this fact is that when a sensor is immersed in a conductive fluid, energy from the sensor will dissipate, substantially lowering the Q and reducing the sensor-to-electronics distance. For example, the sensors described above were immersed in saline (0.9% salt solution), and the measured Q decreased to approximately 10. It has been found that such loss can be minimized by further separation of the sensor from the conductive liquid. This can be accomplished, for example, by encapsulating the sensor in a suitable low-loss-tangent dielectric material. However, potential encapsulation material must have the flexibility and biocompatibility characteristics of the sensor material and also be sufficiently compliant to allow transmission of fluid pressure to the pressure sensitive diaphragm. A preferred material for this application is polydimethylsiloxane (silicone).

As an example, a thin (i.e., 200 micron) coating of silicone was applied to the sensor detailed above. This coating provided sufficient insulation to maintain the Q at 50 in a conductive medium. Equally important, despite the presence of the silicone, adequate sensitivity to pressure changes was maintained and the sensor retained sufficient flexibility to be folded for endovascular delivery. One additional benefit of the silicone encapsulation material is that it can be optionally loaded with a low percentage (i.e., 10-20%) of radio-opaque material (e.g., barium sulfate) to provide visibility when examined using fluoroscopic x-ray equipment. This added barium sulfate will not affect the mechanical and electrical properties of the silicone.

As described above, it is desirable to increase the Q factor of a sensor, and the Q factor can be increased by suitable selection of sensor materials or a coating, or both. Preferably both are used, because the resulting high Q factor of a sensor prepared in this fashion is especially suitable for the applications described.

When introduced into the sac of an abdominal aorta, the pressure sensor can provide pressure related data by use of an external measuring device. As disclosed in the Allen et al. patents, several different excitation systems can be used. The readout device generates electromagnetic energy that can penetrate through the body's tissues to the sensor's implanted location. The sensor's electrical components can absorb a fraction of the electromagnetic energy that is generated by the readout device via inductive coupling. This coupling will induce a current in the sensor's circuit that will oscillate at the same frequency as the applied electromagnetic energy. Due to the nature of the sensor's electromechanical system there will exist a frequency of alternating current at which the absorption of energy from the readout device is at a minimum. This frequency is a function of the capacitance of the device. Therefore, if the sensor's capacitance changes so will the frequency at which it minimally absorbs energy from the readout device. Since the sensor's capacitance is mechanically linked to the fluid pressure at the sensor's surface, a measurement of this frequency by the readout device can give a relative measurement of the fluid pressure. If calibration of the device is performed then an absolute measurement of pressure can be made.

Figure 28:
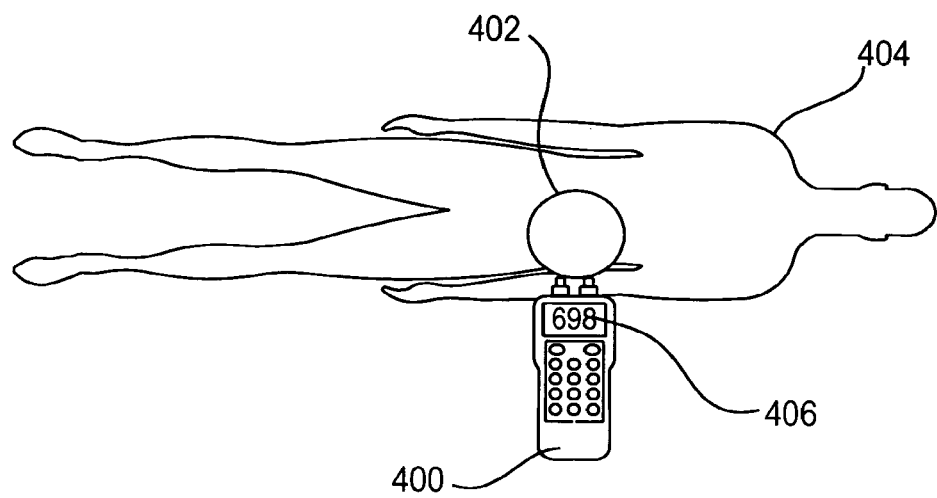
FIG. 28 is a schematic of a control system.

The circuitry used to measure and display pressure is contained within a simple to operate, portable electronic unit 400, as shown in FIG. 28. This unit 400 also contains the antenna 402 needed to perform the electromagnetic coupling to the sensor. The antenna 402 may be integrated into the housing for the electronics or it may be detachable from the unit 400 so that it can be positioned on the surface of the body 404 in proximity to the implanted sensor and easily moved to optimize the coupling between antenna and sensor. The antenna 402 itself may consist of a simple standard coil configuration or may incorporate ferrous elements to maximize the coupling efficiency. The electronic device 400 would feature an LCD or LED display 406 designed to clearly display the recorded pressure in physiologically relevant units such as mm Hg. In an alternative embodiment, the display 406 may be created by integrating a commercially available hand-held computing device such as a Palm® or micro-PC into the electronic circuitry and using this device's display unit as the visual interface between the equipment and its operator. A further advantage of this approach is that the hand-held computer could be detached from the read-out unit and linked to a standard desktop computer. The information from the device could thus be downloaded into any of several commercially available data acquisition software programs for more detailed analysis or for electronic transfer via hard media or the internet to a remote location.

Accordingly, the present invention provides for an impedance system and method of determining the resonant frequency and bandwidth of a resonant circuit within a particular sensor. The system includes a loop antenna, which is coupled to an impedance analyzer. The impedance analyzer applies a constant voltage signal to the loop antenna scanning the frequency across a predetermined spectrum. The current passing through the transmitting antenna experiences a peak at the resonant frequency of the sensor. The resonant frequency and bandwidth are thus determined from this peak in the current.

The method of determining the resonant frequency and bandwidth using an impedance approach may include the steps of transmitting an excitation signal using a transmitting antenna and electromagnetically coupling a sensor having a resonant circuit to the transmitting antenna thereby modifying the impedance of the transmitting antenna. Next, the step of measuring the change in impedance of the transmitting antenna is performed, and finally, the resonant frequency and bandwidth of the sensor circuit are determined.

In addition, the present invention provides for a transmit and receive system and method for determining the resonant frequency and bandwidth of a resonant circuit within a particular sensor. According to this method, an excitation signal of white noise or predetermined multiple frequencies is transmitted from a transmitting antenna, the sensor being electromagnetically coupled to the transmitting antenna. A current is induced in the resonant circuit of the sensor as it absorbs energy from the transmitted excitation signal, the current oscillating at the resonant frequency of the resonant circuit. A receiving antenna, also electromagnetically coupled to the transmitting antenna, receives the excitation signal minus the energy which was absorbed by the sensor. Thus, the power of the received signal experiences a dip or notch at the resonant frequency of the sensor. The resonant frequency and bandwidth are determined from this notch in the power.

The transmit and receive method of determining the resonant frequency and bandwidth of a sensor circuit includes the steps of transmitting a multiple frequency signal from transmitting antenna, and, electromagnetically coupling a resonant circuit on a sensor to the transmitting antenna thereby inducing a current in the sensor circuit. Next, the step of receiving a modified transmitted signal due to the induction of current in the sensor circuit is performed. Finally, the step of determining the resonant frequency and bandwidth from the received signal is executed.

Yet another system and method for determining the resonant frequency and bandwidth of a resonant circuit within a particular sensor includes a chirp interrogation system. This system provides for a transmitting antenna which is electromagnetically coupled to the resonant circuit of the sensor. An excitation signal of white noise or predetermined multiple frequencies, or a time-gated single frequency is applied to the transmitting antenna for a predetermined period of time, thereby inducing a current in the resonant circuit of the sensor at the resonant frequency. The system then listens for a return signal which is coupled back from the sensor. The resonant frequency and bandwidth of the resonant circuit are determined from the return signal.

The chirp interrogation method for determining the resonant frequency and bandwidth of a resonant circuit within a particular sensor includes the steps of transmitting a multi-frequency signal pulse from a transmitting antenna, electromagnetically coupling a resonant circuit on a sensor to the transmitting antenna thereby inducing a current in the sensor circuit, listening for and receiving a return signal radiated from the sensor circuit, and determining the resonant frequency and bandwidth from the return signal.

The present invention also provides an analog system and method for determining the resonant frequency of a resonant circuit within a particular sensor. The analog system comprises a transmitting antenna coupled as part of a tank circuit which in turn is coupled to an oscillator. A signal is generated which oscillates at a frequency determined by the electrical characteristics of the tank circuit. The frequency of this signal is further modified by the electromagnetic coupling of the resonant circuit of a sensor. This signal is applied to a frequency discriminator which in turn provides a signal from which the resonant frequency of the sensor circuit is determined.

The analog method for determining the resonant frequency and bandwidth of a resonant circuit within a particular sensor includes the steps of generating a transmission signal using a tank circuit which includes a transmitting antenna, modifying the frequency of the transmission signal by electromagnetically coupling the resonant circuit of a sensor to the transmitting antenna, and converting the modified transmission signal into a standard signal for further application.

The invention further includes an alternative method of measuring pressure in which a non-linear element such as a diode or polyvinylidenedifluoride piezo-electric polymer is added to the LC circuit. A diode with a low turn-on voltage such as a Schottky diode can be fabricated using micromachining techniques. The presence of this non-linear element in various configurations within the LC circuit can be used to modulate the incoming signal from the receiving device and produce different harmonics of the original signal. The read-out circuitry can be tuned to receive the particular harmonic frequency that is produced and use this signal to reconstruct the fundamental frequency of the sensor. The advantage of this approach is two-fold; the incoming signal can be transmitted continuously and since the return signal will be at different signals, the return signal can also be received continuously.

The above methods lend themselves to the creation of small and simple to manufacture hand-held electronic devices that can be used without complication.

The preceding specific embodiments are illustrative of the practice of the invention. It is to be understood, however, that other expedients known to those skilled in the art or disclosed herein, may be employed without departing from the spirit of the invention of the scope of the appended claims.

We claim:

1. A wireless sensor for indicating a physical property of an environment, comprising:
 a housing comprising:
  a first substrate having a first wall and a peripheral edge; and
  a second, opposed substrate having a second wall and a peripheral edge, wherein the peripheral edge of the first substrate and the peripheral edge of the second substrate are homogenously and sealingly fused along a peripheral heat effect zone to define a hermetic chamber having the first and second walls spaced opposition, wherein the heat effect zone is spaced from the hermetic chamber, and wherein the first and second substrates are formed from the same dielectric material, and wherein the housing is homogeneous; and
 a structure located within the hermetic chamber of the housing comprising:
  at least a pair of opposed capacitance elements providing capacitance, the pair of capacitance elements being mounted on the first and second walls of the hermetic chamber and spaced apart from one another by at least one distance, the pair of capacitance elements being arranged such that the at least one distance and thereby the capacitance of the structure changes when the physical property of the environment changes; and
  at least one inductance element operatively coupled to the pair of capacitance elements,
  wherein the structure has a resonant frequency based at least in part on the capacitance of the structure when the structure is in the presence of a fluctuating electromagnetic field,
  whereby, when the sensor is positioned within an environment and is in the presence of a fluctuating electromagnetic field, the resonant frequency indicates the physical property of the environment.

2. The sensor of claim 1, wherein at least one of the first and second walls of the hermetic chamber has a portion of reduced thickness relative to the remaining walls defining the hermetic chamber such that the at least one wall deforms in response to a predetermined range of environmental pressure.

3. The sensor of claim 1, wherein the housing comprises a material selected from the group consisting of glass, fused silica, sapphire, and quartz.

4. The sensor of claim 1, wherein the physical property is pressure.

5. The sensor of claim 1, wherein the at least one inductance element comprises an opposed pair of inductance elements.

6. The sensor of claim 1, wherein the at least one inductance element comprises at least one wire spiral.

7. The sensor of claim 1, wherein the housing is from about 0.5 in. to about 1 in. in length and from about 0.1 in. to about 0.5 in. in width.

8. The sensor of claim 7, wherein the housing has a thickness of from about 0.05 in. to about 0.30 in.

9. The sensor of claim 1, further comprising a stabilizer operatively associated with the sensor for stabilizing the sensor within the body of a patient.

10. The sensor of claim 9, wherein the stabilizer stabilizes at least one of position, location, and orientation of the sensor.

11. The sensor of claim 9, wherein the stabilizer comprises at least one wire arranged around the outer surface of the sensor.

12. The sensor of claim 11, wherein the at least one wire comprises a wire basket.

13. The sensor of claim 1, wherein the housing is substantially impervious to the passage of atoms and molecules into and out of the hermetic chamber.

14. The sensor of claim 1, wherein the housing comprises a material which elicits a medically acceptable level of biological reaction.

15. The sensor of claim 1, wherein the sensor further comprises a polymer coating applied to the exterior of the housing.

16. The sensor of claim 15, wherein the polymer coating comprises silicone.

17. The sensor of claim 6, wherein the at least one wire spiral comprises at least one oblong wire spiral.

18. A wireless sensor for indicating a physical property of an environment, comprising:
- a housing comprising:
  - a first substrate having a first wall and a peripheral edge; and
  - a second, opposed substrate having a second wall and a peripheral edge, wherein the peripheral edge of the first substrate and the peripheral edge of the second substrate are homogenously and sealingly fused, wherein the first and second substrates are comprised of the same dielectric material, and wherein the housing is homogeneous; and
- a structure located within the hermetic chamber of the housing comprising:
  - at least a pair of opposed capacitance elements providing capacitance, the pair of capacitance elements being mounted on the first and second walls of the hermetic chamber and spaced apart from one another by at least one distance, the pair of capacitance elements being arranged such that the at least one distance and thereby the capacitance of the structure changes when the physical property of the environment changes; and
  - at least one inductance element operatively coupled to the pair of capacitance elements,
  - wherein the structure has a resonant frequency based at least in part on the capacitance of the structure when the structure is in the presence of a fluctuating electromagnetic field,
- whereby, when the sensor is positioned within an environment and is in the presence of a fluctuating electromagnetic field, the resonant frequency indicates the physical property of the environment.

19. A wireless sensor for indicating a physical property of an environment, comprising:
- a housing comprising:
  - a first substrate having a first wall and a peripheral edge; and
  - a second, opposed substrate having a second wall and a peripheral edge, n the peripheral edge of the first substrate and the peripheral edge of the second substrate are homogenously and sealingly fused along a peripheral heat effect zone to define a hermetic chamber having the first and second walls in spaced opposition, wherein the heat effect zone is spaced from the hermetic chamber; and
- a structure located within the hermetic chamber of the housing comprising:
  - at least a pair of opposed capacitance elements providing capacitance, the pair of capacitance elements being mounted on the first and second walls of the hermetic chamber and spaced apart from one another by at least one distance, the pair of capacitance elements being arranged such that the at least one distance and thereby the capacitance of the structure changes when the physical property of the environment changes; and
  - at least one inductance element operatively coupled to the pair of capacitance elements,
  - wherein the structure has a resonant frequency based at least in part on the capacitance of the structure when the structure is in the presence of a fluctuating electromagnetic field,
- whereby, when the sensor is positioned within an environment and is in the presence of a fluctuating electromagnetic field, the resonant frequency indicates the physical property of the environment.

\* \* \* \* \*